United States Patent
Yang et al.

(10) Patent No.: US 12,369,569 B1
(45) Date of Patent: Jul. 29, 2025

(54) METHOD FOR GENERATING GENOME-EDITED CHICKENS

(71) Applicant: CHINA AGRICULTURAL UNIVERSITY, Beijing (CN)

(72) Inventors: Ning Yang, Beijing (CN); Xiqiong Wang, Beijing (CN); Congjiao Sun, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 0 days.

(21) Appl. No.: 18/984,398

(22) Filed: Dec. 17, 2024

Related U.S. Application Data

(63) Continuation of application No. PCT/CN2024/106891, filed on Jul. 23, 2024.

(30) Foreign Application Priority Data

Jul. 12, 2024 (CN) .......................... 202410931448.9

(51) Int. Cl.
*A01K 67/0275* (2024.01)
*C12N 9/22* (2006.01)
*C12N 15/11* (2006.01)

(52) U.S. Cl.
CPC ............ *A01K 67/0275* (2013.01); *C12N 9/22* (2013.01); *C12N 15/111* (2013.01); *A01K 2227/30* (2013.01); *C12N 2310/20* (2017.05)

(58) Field of Classification Search
CPC .. A01K 67/0275; A01K 2227/30; C12N 9/22; C12N 2310/20
See application file for complete search history.

(56) References Cited

U.S. PATENT DOCUMENTS

2022/0136003 A1    5/2022    Cinnamon et al.

FOREIGN PATENT DOCUMENTS

| CN | 1654668 | A |   | 8/2005 |
| CN | 100343391 | C | * | 10/2007 |
| CN | 109897867 | A |   | 7/2021 |
| CN | 113151277 | A |   | 7/2021 |
| CN | 113692225 | A |   | 11/2021 |
| KR | 102270145 | B1 |  | 7/2021 |

OTHER PUBLICATIONS

Puchta et al (CRISPR/Cas9 gene editing in a chicken model: current approaches and applications. Journal of Applied Genetics (2020) 61:221-229; cited in IDS dated Dec. 17, 2024) (Year: 2020).*

Rasys et al (CRISPR-Cas9 Gene Editing in Lizards through Microinjection of Unfertilized Oocytes. Cell Reports 28, 2288-2292, Aug. 2019 (Year: 2019).*
Jiang et al (Generation of transgenic chicken through ovarian injection. Anim Models Exp Med. 2025;8:187-193. First published: Dec. 27, 2024) (Year: 2024).*
IDT Alt-R CRISPR-Cas9 Genome editing (Genome editing with CRISPR-Cas9 <<https://www.idtdna.com/pages/products/crispr-genome-editing/alt-r-crispr-cas9-system>> (Year: 2019).*
Hoshijima et al (Highly Efficient CRISPR-Cas9-Based Methods for Generating Deletion Mutations and F0 Embryos that Lack Gene Function in Zebrafish. Developmental Cell 51, 645-657, 2019). (Year: 2019).*
Vortkamp et al (Regulation of rate of cartilage differentiation by Indian hedgehog and PTH-related protein. Science, vol. 273, 1996). (Year: 1996).*
Ashley, VA (The Importance of Fasting Before Surgery. Riverview Animal Health Centre Jun. 20, 2019). (Year: 2019).*
Punnett (Heredity in Poultry. Macmillan and Co., 1923). (Year: 1923).*
Liu et al (CN 100343391C, Machine Translation (Year: 2025).*
Sequence alignment SEQ ID 3 with IHH gene from Vortkamp (Year: 1996).*
CRISPT/Cas9 gene editing in a chicken model: current approaches and applications, Journal of Applied Genetics, 2020.
CNIPA, Office Action, Application No. 202410931448.9, Aug. 14, 2024.
Abe, T. et al., "A reverse genetic approach in geckos with the CRISPER/Cas9 system by oocyte microinjection", Developmental Biology497, 2023.
Wu, X. et al., "The genetic program of oocytes can be modified in vivo in the zebrafish ovary", Journal of Molecular Cell Biology (2018), 10(6), 479-493.
Iwaizumi, M. et al., "Delivery of exogenous proteins into eggs by injection into the mother's ovary (IMO) in zebrafish", Fish Physiol Biochem, 2021.
Chojnacka-Puchta, L. & Sawicka, D., "CRISPR/Cas9 gene editing in a chicken model: current approaches and applications".
Chen, C. et al., "Progress of CRISPR/Cas9 Technology in Chicken Genetic Breeding", China Poultry vol. 45 , No. 6.2023, Only Abstract in english.

* cited by examiner

*Primary Examiner* — Emily A Cordas
*Assistant Examiner* — Matasha Dhar
(74) *Attorney, Agent, or Firm* — WCF IP

(57) ABSTRACT

A method for generating a genome-edited chicken is provided, relating to the technical field of genetic engineering. Ovarian injection in situ is conducted on a hen, where a gene editing reagent is injected into ovarian medulla of the hen that is close to laying eggs, such that the exogenously-injected gene editing reagent can enter developing ovarian follicles through blood circulation. In resulting Go individuals, a chimera chicken with both somatic cells and germ cells edited is successfully and efficiently obtained, with an editing efficiency of the Go individuals reaching up to 36.36%. Compared with a traditional primordial germ cell (PGC)-mediated method, the ovarian injection in situ is time-saving and labor-saving, convenient and rapid, low-cost, and highly safe.

10 Claims, 21 Drawing Sheets
Specification includes a Sequence Listing.

A
| | | gRNA | PAM | |
|---|---|---|---|---|
| IHH-gRNA-R2 | 5'-CCCCGGCGGCGGCAATAAATAGCGAAGGGCCGTTT-3' | | | SEQ ID NO: 38 |
| IHH-gRNA-R3 | 5'-TTGTAGGCGAGCGGGATGAGCTTGCGGGGCGGCCG-3' | | | SEQ ID NO: 39 |
| IHH-gRNA-R1 | 5'-GGGCCGTACCTGGGTCATGAGCCGGTCGGCGCCGG-3' | | | SEQ ID NO: 40 |
FIG. 1A
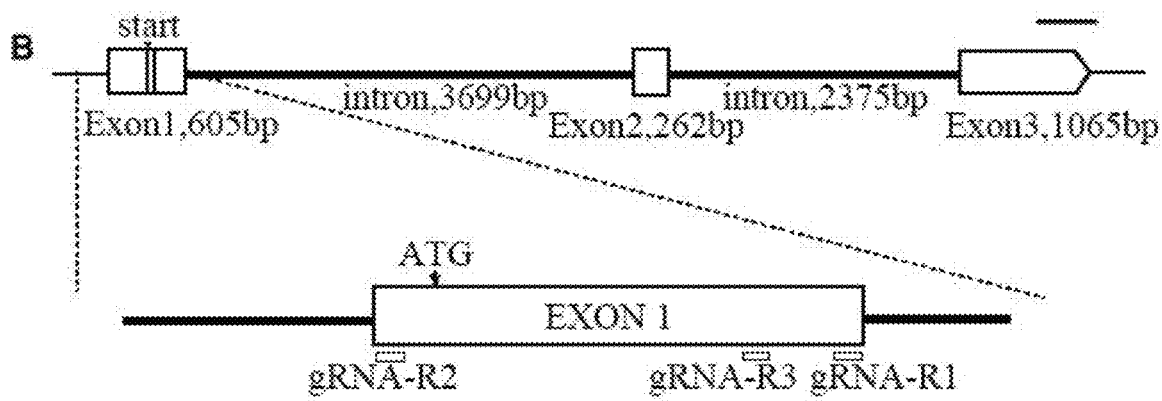
FIG. 1B
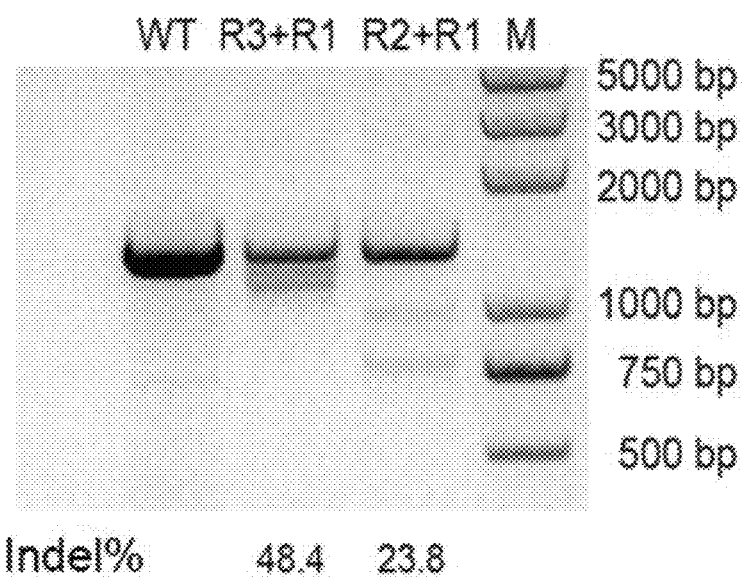
FIG. 1C

```
GCCGTGCGCTGCTGCGGGCCGG GCAGCGTTGT GGGCAGCCGC CGCCGGCCG
++++++++++++++++++++++++++++++++++++++++++++++++++++
CGGCACGCGACGACGCCCGGCC CGTCCCAACA CCCGTCGGCG GCGGCCGGC
     20           25              30               35
Ala Val Arg Cys Cys Gly Pro    Gly Arg Val Val  Gly Ser Arg  Arg Arg Pro
                                IHH
                               exon 1
```

FIG. 3B (con't)

```
CCCCGCAAGCTCATCCCGCTCGCCTACAAGCAGTTCAGCCCCAACGTGCC  SEQ ID
++++++++++++++++++++++++++++++++++++++++++++++++++  NO: 41
GGGGCGTTCGAGTAGGGCGAGCGGATGTTCGTCAAGTCGGGGTTGCACGG  SEQ ID
        40           45              50              NO: 42
Pro Arg Lys Leu Ile Pro Leu Ala Tyr Lys Gln Phe Ser Pro Asn Val Pro  SEQ ID
                                                                     NO: 44

┌─────────────────────────┐
 │GCGTTCGAGTAGGGCGAGCCG│ SEQ ID NO: 43
 └─────────────────────────┘
        sgRNA R3
```

FIG. 3B (con't)

3-28-3 1/17

3-28-4 1/17

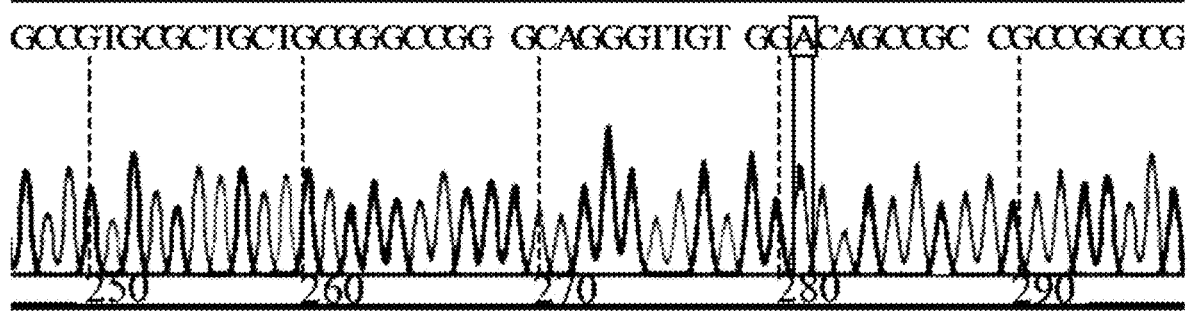
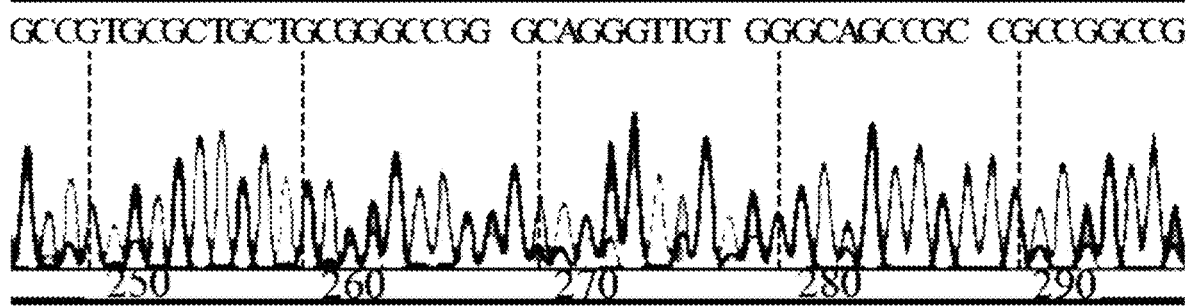
FIG. 3C (con't)

3-28-3 1/17
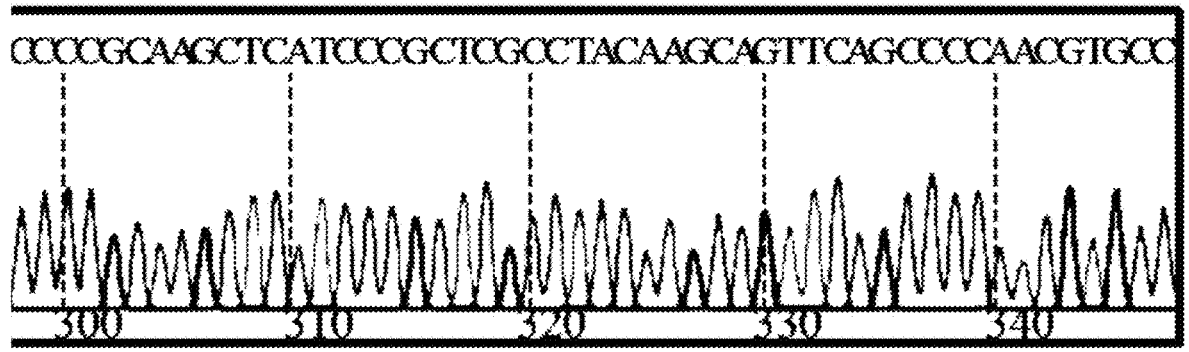
3-28-4 1/17
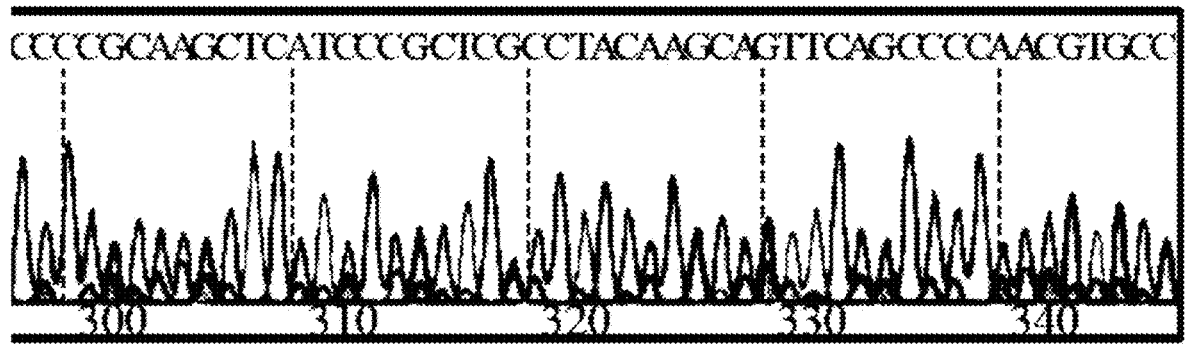
FIG. 3C (con't)

4-22-2 1/20

4-22-3 1/20

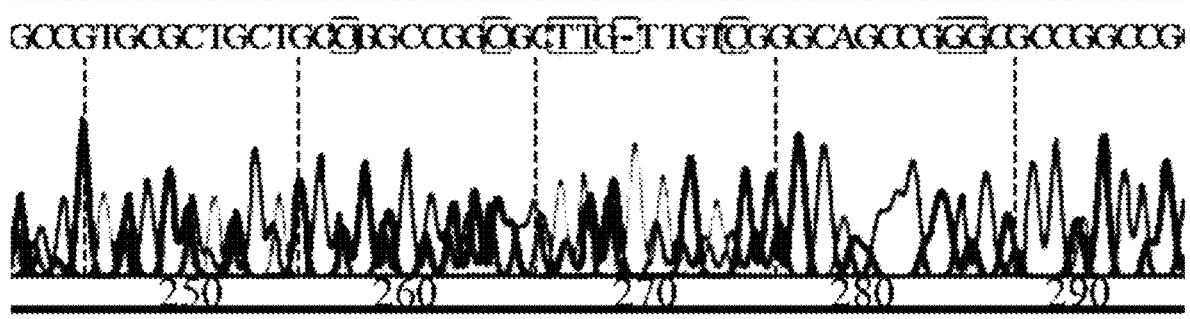
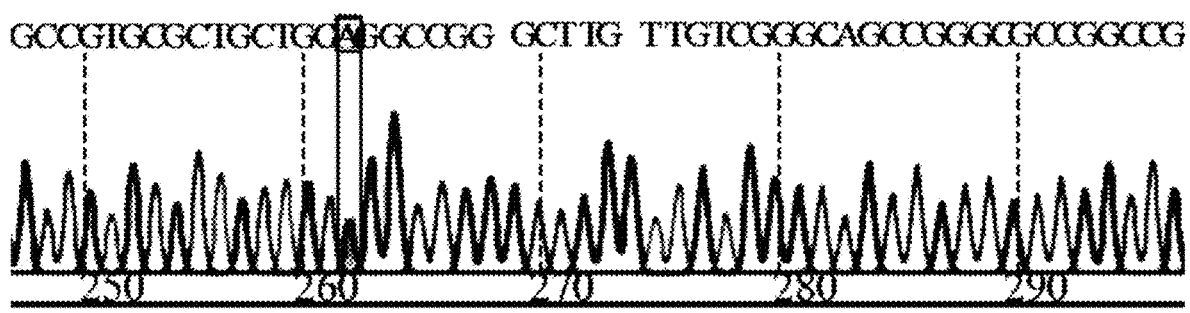
FIG. 3D (con't)

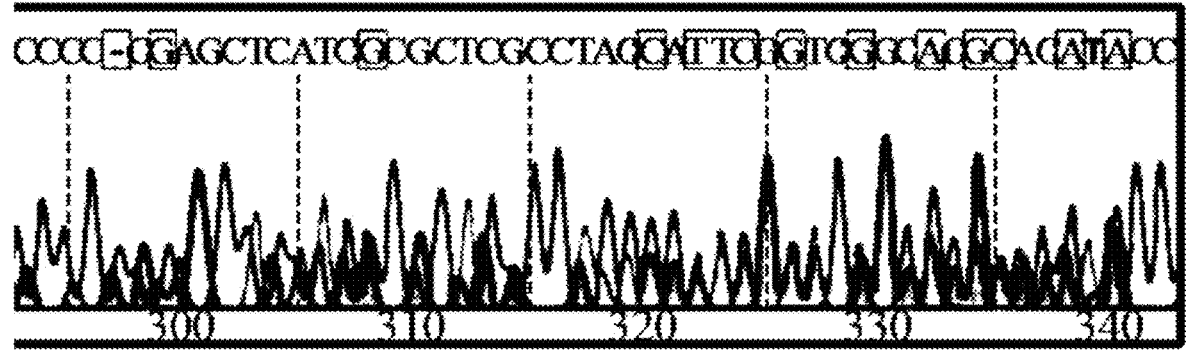
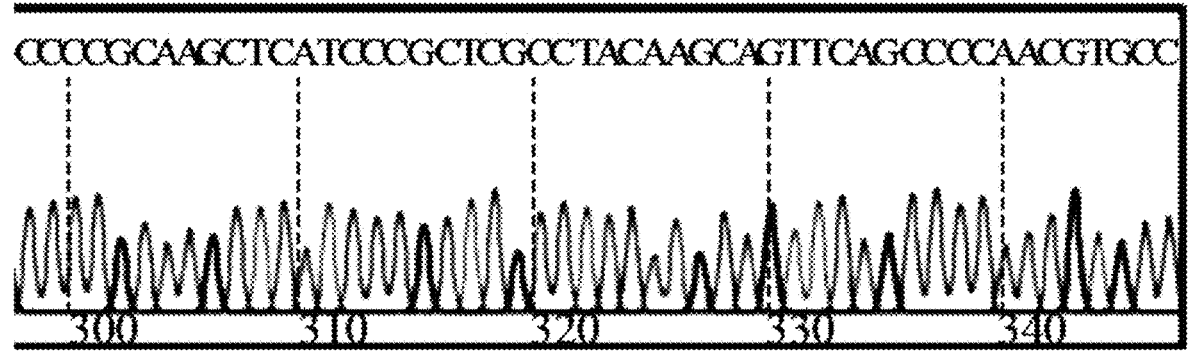
FIG. 3D (con't)

```
CCGGCCGTGCCCTGCTGCGGCCGG GCAGGGTTGT GGCCAGCCGC CGCCGGCCG
||||||||||||||||||||||||||||||||||||||||||||||||||||||
GGCCGGCACGCGACGACGCCGGCC CGTCCCAACA CCGGTCGGCG GCGGCCGGC
        20           25              30              35
  Pro Ala Val ArgCys CysGly Pro  Gly Arg ValVal  Gly Ser Arg  Arg Arg Pro
                              IHH →
                         exon 1
```

FIG. 5C (con't)

```
CCCCGCAAGCTCATCCCGCTCGCCTACAAGCAGTTCAGCCCCAACGTGCC
||||||||||||||||||||||||||||||||||||||||||||||||||
GGGGCGTTCGAGTAGGGCGAGCGGATGTTCGTCAAGTCGGGGTTGCACGG
       40              45              50
 Pro Arg Lys Leu Ile Pro Leu Ala Thr Lys Gln Phe Ser  Pro Asn ValPro

GCGTTCGAGTAGGGCGAGCG
                   sgRNA R3
```

FIG. 5C (con't)

50981-gonad 1/13

50981-gonad 1/13

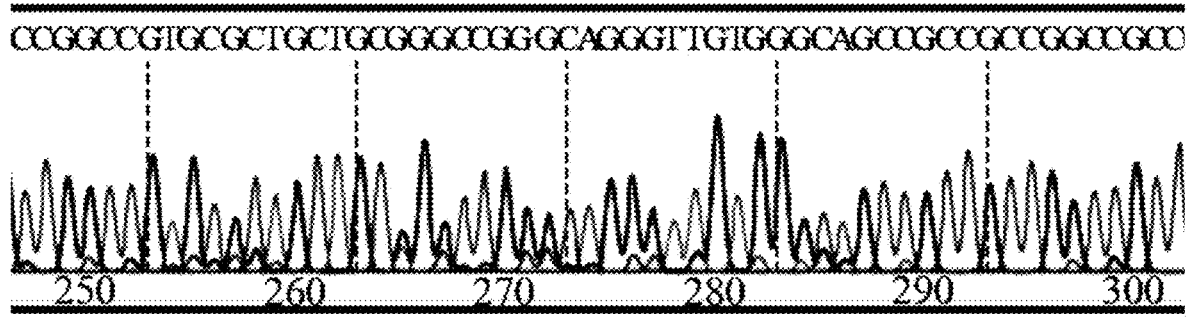
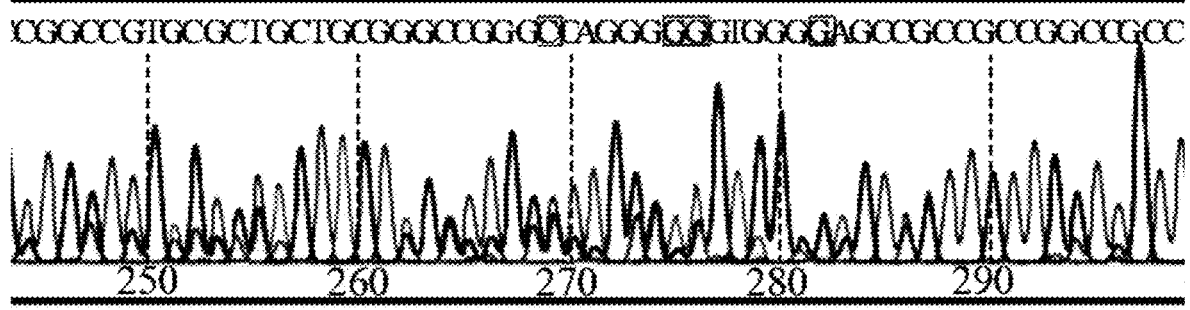
FIG. 5D (con't)

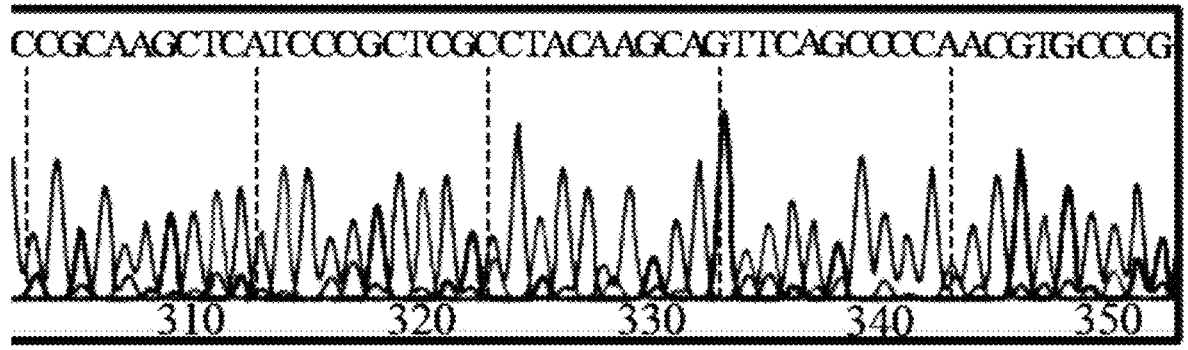
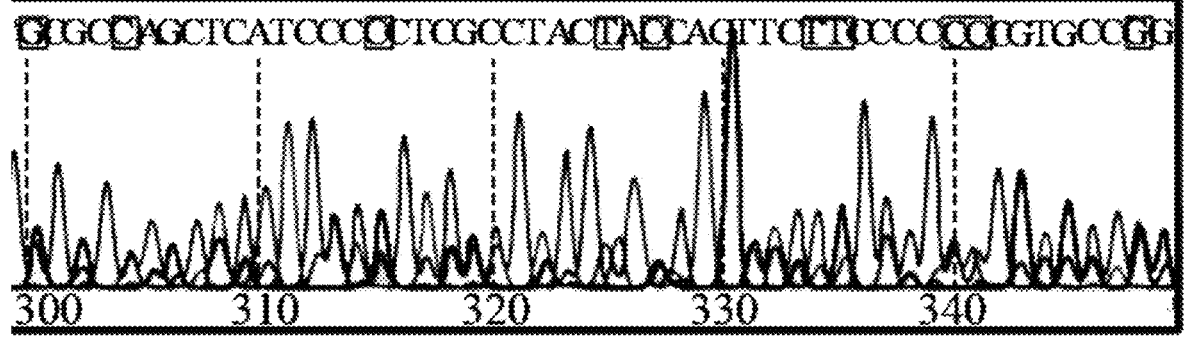
FIG. 5D (con't)

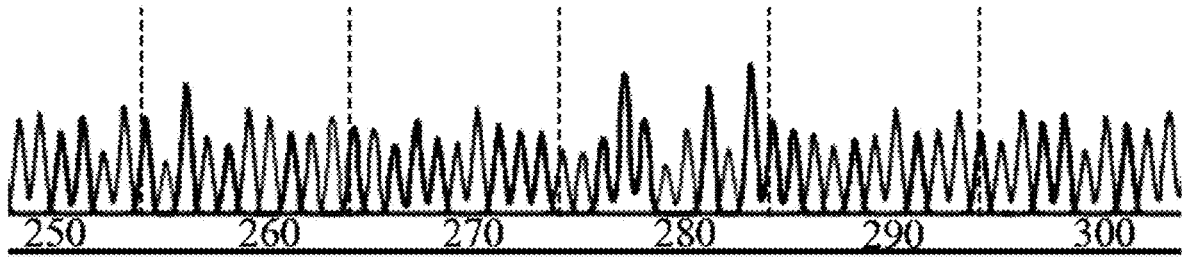
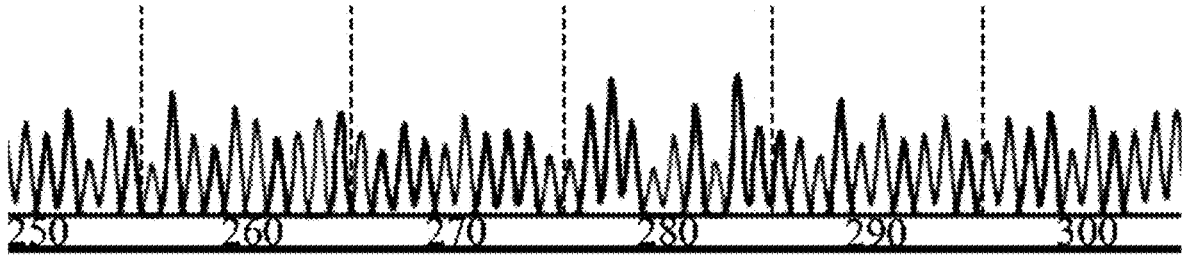
FIG. 5E (con't)

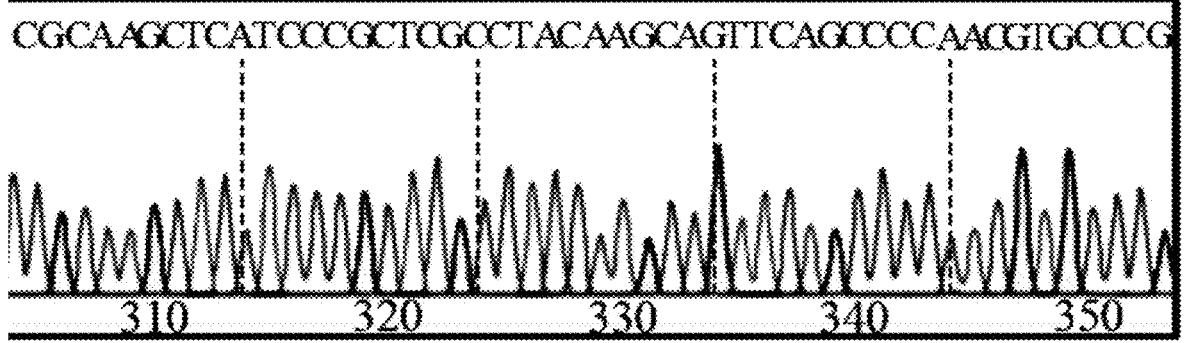
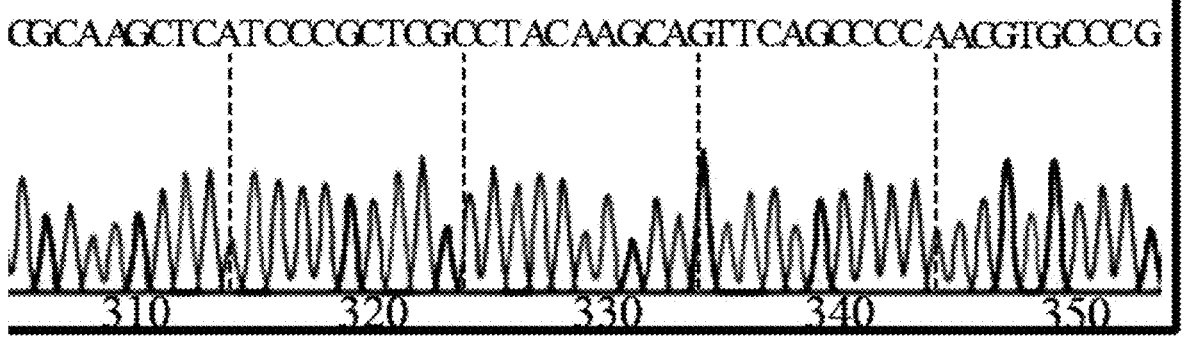
FIG. 5E (con't)

SEQUENCE LISTING

```
Sequence total quantity: 51
SEQ ID NO: 1               moltype = DNA  length = 20
FEATURE                    Location/Qualifiers
source                     1..20
                           mol_type = other DNA
                           note = Sequence of gRNA-R1
                           organism = synthetic construct
SEQUENCE: 1
tacctgggtc atgagccggt                                                   20

SEQ ID NO: 2               moltype = DNA  length = 20
FEATURE                    Location/Qualifiers
source                     1..20
                           mol_type = other DNA
                           note = Sequence of gRNA-R2
                           organism = synthetic construct
SEQUENCE: 2
cggcggcaat aaatagcgaa                                                   20

SEQ ID NO: 3               moltype = DNA  length = 20
FEATURE                    Location/Qualifiers
source                     1..20
                           mol_type = other DNA
                           note = Sequence of gRNA-R3
                           organism = synthetic construct
SEQUENCE: 3
gcgagcggga tgagcttgcg                                                   20

SEQ ID NO: 4               moltype = DNA  length = 405
FEATURE                    Location/Qualifiers
source                     1..405
                           mol_type = other DNA
                           note = element sequence that could transcribe the dual
                             gRNAs (for IHH-gR2+gR1)
                           organism = synthetic construct
SEQUENCE: 4
atcggaagac ctcaccgcgg cggcaataaa tagcgaagtt ttagagctag aaatagcaag       60
ttaaaataag gctagtccgt tatcaacttg aaaaagtggc accgagtcgg tgcttttttg      120
agggcctatt tcccatgatt ccttcatatt tgcatatacg atacaaggct gttagagaga      180
taattggaat taatttgact gtaaacacaa agatattagt acaaaatacg tgacgtagaa      240
agtaataatt tcttgggtag tttgcagttt taaaattatg ttttaaaatg gactatcata      300
tgcttaccgt aacttgaaag tatttcgatt tcttggcttt atatatcttg tggaaggac       360
```

```
gaaacaccgt acctgggtca tgagccggtg tttgggtctt catcg           405

SEQ ID NO: 5            moltype = DNA   length = 404
FEATURE                 Location/Qualifiers
source                  1..404
                        mol_type = other DNA
                        note = element sequence that could transcribe the dual
                          gRNAs (for IHH-gR3+gR1)
                        organism = synthetic construct
SEQUENCE: 5
atcggaagac ctcaccgcga gcgggatgag cttgcggttt tagagctaga aatagcaagt   60
taaaataagg ctagtccgtt atcaacttga aaaagtggca ccgagtcggt gcttttttga  120
gggcctattt cccatgattc cttcatattt gcatatacga tacaaggctg ttagagagat  180
aattggaatt aatttgactg taaacacaaa gatattagta caaaatacgt gacgtagaaa  240
gtaataattt cttgggtagt ttgcagtttt aaaattatgt tttaaaatgg actatcatat  300
gcttaccgta acttgaaagt atttcgattt cttggcttta tatatcttgt ggaaaggacg  360
aaacaccgta cctgggtcat gagccggtgt ttgggtcttc atcg                   404

SEQ ID NO: 6            moltype = DNA   length = 56
FEATURE                 Location/Qualifiers
source                  1..56
                        mol_type = other DNA
                        note = Sequence of primer IHH-gR2+gR1-F
                        organism = synthetic construct
SEQUENCE: 6
atcggaagac ctcaccgcgg cggcaataaa tagcgaagtt ttagagctag aaatag       56

SEQ ID NO: 7            moltype = DNA   length = 54
FEATURE                 Location/Qualifiers
source                  1..54
                        mol_type = other DNA
                        note = Sequence of IHH-gR2+gR1-R
                        organism = synthetic construct
SEQUENCE: 7
cgatgaagac ccaaacaccg gctcatgacc caggtacggt gtttcgtcct ttcc         54

SEQ ID NO: 8            moltype = DNA   length = 55
FEATURE                 Location/Qualifiers
source                  1..55
                        mol_type = other DNA
                        note = Sequence of IHH-gR3+gR1-F
                        organism = synthetic construct
SEQUENCE: 8
atcggaagac ctcaccgcga gcgggatgag cttgcggttt tagagctaga aatag        55

SEQ ID NO: 9            moltype = DNA   length = 18
FEATURE                 Location/Qualifiers
source                  1..18
                        mol_type = other DNA
                        note = Forward primer designed for the target sequences and
                          PCR
                        organism = synthetic construct
SEQUENCE: 9
aatttcccct ctcactcc                                                 18

SEQ ID NO: 10           moltype = DNA   length = 18
FEATURE                 Location/Qualifiers
source                  1..18
                        mol_type = other DNA
                        note = Reverse primer designed for the target sequences and
                          PCR
                        organism = synthetic construct
SEQUENCE: 10
ctttgccatc ctactctg                                                 18

SEQ ID NO: 11           moltype = DNA   length = 40
FEATURE                 Location/Qualifiers
source                  1..40
                        mol_type = other DNA
                        note = Primer T7_IHH_gR1_F
                        organism = synthetic construct
SEQUENCE: 11
taatacgact cactataggg tacctgggtc atgagccggt                         40

SEQ ID NO: 12           moltype = DNA   length = 40
FEATURE                 Location/Qualifiers
source                  1..40
                        mol_type = other DNA
                        note = Primer T7_IHH-gR3_F
```

```
                                    organism = synthetic construct
SEQUENCE: 12
taatacgact cactataggg gcgagcggga tgagcttgcg                         40

SEQ ID NO: 13           moltype = DNA  length = 24
FEATURE                 Location/Qualifiers
source                  1..24
                        mol_type = other DNA
                        note = Primer T7_uni_R
                        organism = synthetic construct
SEQUENCE: 13
aaaaaagcac cgactcggtg ccac                                          24

SEQ ID NO: 14           moltype = DNA  length = 20
FEATURE                 Location/Qualifiers
source                  1..20
                        mol_type = other DNA
                        note = T7 promoter sequence
                        organism = synthetic construct
SEQUENCE: 14
taatacgact cactataggg                                               20

SEQ ID NO: 15           moltype = DNA  length = 18
FEATURE                 Location/Qualifiers
source                  1..18
                        mol_type = other DNA
                        note = transcription termination sequence
                        organism = synthetic construct
SEQUENCE: 15
gcaccgactc ggtgccac                                                 18

SEQ ID NO: 16           moltype = DNA  length = 41
FEATURE                 Location/Qualifiers
source                  1..41
                        mol_type = other DNA
                        note = primers Cas9-tyF
                        organism = synthetic construct
SEQUENCE: 16
caagcgcatg ctggccagcg ccggcgagct gcagaagggc a                       41

SEQ ID NO: 17           moltype = DNA  length = 38
FEATURE                 Location/Qualifiers
source                  1..38
                        mol_type = other DNA
                        note = Cas9-tyR
                        organism = synthetic construct
SEQUENCE: 17
tctcgtacag accggtgatg ctctggtgga tcagggtg                           38

SEQ ID NO: 18           moltype = DNA  length = 160
FEATURE                 Location/Qualifiers
source                  1..160
                        mol_type = other DNA
                        note = 2NLS sequence
                        organism = synthetic construct
SEQUENCE: 18
catcaccggt ctgtacgaga cccgcatcga cctgagccag ctgggcggcg acggcggctc   60
cggacctcca aagaaaaaga gaaaagtaga ggacccaaag aaaaagagaa agtataccc   120
ctacgacgtg cccgactacg cctgttaact cgagcaccac                        160

SEQ ID NO: 19           moltype = DNA  length = 35
FEATURE                 Location/Qualifiers
source                  1..35
                        mol_type = other DNA
                        note = primers 2NLS-tyF
                        organism = synthetic construct
SEQUENCE: 19
catcaccggt ctgtacgaga cccgcatcga cctga                              35

SEQ ID NO: 20           moltype = DNA  length = 43
FEATURE                 Location/Qualifiers
source                  1..43
                        mol_type = other DNA
                        note = 2NLS-tyR
                        organism = synthetic construct
SEQUENCE: 20
cagtggtggt ggtggtggtg ctcgagttaa caggcgtagt cgg                     43

SEQ ID NO: 21           moltype = DNA  length = 18
```

```
FEATURE                    Location/Qualifiers
source                     1..18
                           mol_type = other DNA
                           note = Forward primer for amplifying the IHH-gR3 target site
                           organism = synthetic construct
SEQUENCE: 21
gcccttcgct atttattg                                                      18

SEQ ID NO: 22              moltype = DNA   length = 18
FEATURE                    Location/Qualifiers
source                     1..18
                           mol_type = other DNA
                           note = Reverse primer for amplifying the IHH-gR3 target site
                           organism = synthetic construct
SEQUENCE: 22
cgtgagctcc ttgaagcg                                                      18

SEQ ID NO: 23              moltype = DNA   length = 22
FEATURE                    Location/Qualifiers
source                     1..22
                           mol_type = other DNA
                           note = Forward primer for amplifying genomic DNA of the
                             individuals with mutations
                           organism = synthetic construct
SEQUENCE: 23
gcccttcgct atttattgcc gc                                                 22

SEQ ID NO: 24              moltype = DNA   length = 23
FEATURE                    Location/Qualifiers
source                     1..23
                           mol_type = other DNA
                           note = Reverse primer for amplifying genomic DNA of the
                             individuals with mutations
                           organism = synthetic construct
SEQUENCE: 24
ggataaactc gctgctctgc cca                                                23

SEQ ID NO: 25              moltype = DNA   length = 22
FEATURE                    Location/Qualifiers
source                     1..22
                           mol_type = other DNA
                           note = Primer Cas9-F
                           organism = synthetic construct
SEQUENCE: 25
cctgagcgaa ctggataagg cc                                                 22

SEQ ID NO: 26              moltype = DNA   length = 22
FEATURE                    Location/Qualifiers
source                     1..22
                           mol_type = other DNA
                           note = Primer Cas9-R
                           organism = synthetic construct
SEQUENCE: 26
ctcttggcga tcatcttccg ca                                                 22

SEQ ID NO: 27              moltype = DNA   length = 21
FEATURE                    Location/Qualifiers
source                     1..21
                           mol_type = other DNA
                           note = IHH-gR1-F2
                           organism = synthetic construct
SEQUENCE: 27
gctcatcccg ctcgcctaca a                                                  21

SEQ ID NO: 28              moltype = DNA   length = 23
FEATURE                    Location/Qualifiers
source                     1..23
                           mol_type = other DNA
                           note = IHH-gR2-F
                           organism = synthetic construct
SEQUENCE: 28
atctcttcaa tttcccctct cac                                                23

SEQ ID NO: 29              moltype = DNA   length = 23
FEATURE                    Location/Qualifiers
source                     1..23
                           mol_type = other DNA
                           note = IHH-gR2-R
                           organism = synthetic construct
```

```
SEQUENCE: 29
gcacccgctc agcagcagca gca                                              23

SEQ ID NO: 30            moltype = DNA  length = 193
FEATURE                  Location/Qualifiers
source                   1..193
                         mol_type = other DNA
                         note = Sequence of 4NLS
                         organism = synthetic construct
SEQUENCE: 30
cagcccatatg cccaagaaaa agcgcaaagt gggtggcagc cgaagaaga agcgcaaagt       60
gggcggcagt ccgaaaaaga aacgcaaagt gggcggtagc ccgaagaaga agcgcaaagt      120
gggtatccac ggtgtcccag cagccaccat ggacaagaag tacagcatcg gcctggacat     180
cggtaccaac agc                                                        193

SEQ ID NO: 31            moltype = DNA  length = 29
FEATURE                  Location/Qualifiers
source                   1..29
                         mol_type = other DNA
                         note = Primer 4NLS-F
                         organism = synthetic construct
SEQUENCE: 31
ggaattccat atgcccaaga aaaagcgca                                        29

SEQ ID NO: 32            moltype = DNA  length = 23
FEATURE                  Location/Qualifiers
source                   1..23
                         mol_type = other DNA
                         note = Primer 4NLS-R
                         organism = synthetic construct
SEQUENCE: 32
cggggtaccg atgtccaggc cga                                              23

SEQ ID NO: 33            moltype = DNA  length = 58
FEATURE                  Location/Qualifiers
source                   1..58
                         mol_type = other DNA
                         note = Primer Cas9-mNG-CR
                         organism = synthetic construct
SEQUENCE: 33
gtcgtagggg tatactttc tcttttcttt tgggtcctct actttctct ttttctttt         58

SEQ ID NO: 34            moltype = AA   length = 5
FEATURE                  Location/Qualifiers
source                   1..5
                         mol_type = protein
                         note = Flexible linker G4S
                         organism = synthetic construct
SEQUENCE: 34
GGGGS                                                                   5

SEQ ID NO: 35            moltype = DNA  length = 759
FEATURE                  Location/Qualifiers
source                   1..759
                         mol_type = other DNA
                         note = G4S*2-mNG-NLS
                         organism = synthetic construct
SEQUENCE: 35
ggtggtggcg gtagcggcgg cggcggtagt atggtcagca aaggcgaaga ggacaacatg       60
gcaagtctgc cggcaaccca cgaactgcat attttggca gcatcaacgg cgtcgacttc      120
gatatggtag tcaaggtac cggtaatccg aacgacggtt acgaagagct gaacctgaag      180
agcaccaaag gcgatctgca atttagtccg tggattctgg ttccgcacat ggttacggc      240
ttccatcagt atctgccgta tccggacggt atgagtccgt tcaggcagc gatggtagat      300
ggttctggtt atcaggtcca tcgtaccatg cagtttgaag atggcgcaag tctgaccgtt      360
aactatcgct acacctacga aggcagccat atcaaggcg aagcgcaggt taaaggtacc      420
ggttttccgg ctgacggtcc ggttatgacc aatagtctga ccgctgctga ttggtgtcgt      480
agcaaaaaga cctacccgaa cgacaagacc atcatctcca ccttcaagtg gagctacacc      540
accggtaacg gtaaacgcta tcgtagtacc gcacgtacca cctataccdtt tgctaaaccg      600
atggcggcga actatctgaa aaaccaaccg atgtacgtct tccgcaagac cgaactgaag      660
cacagcaaaa ccgagctgaa cttcaaagaa tggcagaaag cgttcaccga cgttatgggt      720
atggacgaac tgtacaagcc gaagaagaag cgcaaagtg                             759

SEQ ID NO: 36            moltype = DNA  length = 59
FEATURE                  Location/Qualifiers
source                   1..59
                         mol_type = other DNA
                         note = Cas9-mNG-mF
                         organism = synthetic construct
SEQUENCE: 36
```

```
gaaaagtata cccctacgac gtgcccgact acgcctgtgg tggtggcggt agcggcggc    59

SEQ ID NO: 37          moltype = DNA   length = 59
FEATURE                Location/Qualifiers
source                 1..59
                       mol_type = other DNA
                       note = Cas9-mNG-mR
                       organism = synthetic construct
SEQUENCE: 37
ggtggtggtg gtggtgctcg agcactttgc gcttcttctt cggcttgtac agttcgtcc    59

SEQ ID NO: 38          moltype = DNA   length = 35
FEATURE                Location/Qualifiers
misc_feature           1..35
                       note = IHH-gRNA-R2
source                 1..35
                       mol_type = other DNA
                       organism = synthetic construct
SEQUENCE: 38
ccccggcggc ggcaataaat agcgaagggc cgttt                              35

SEQ ID NO: 39          moltype = DNA   length = 35
FEATURE                Location/Qualifiers
misc_feature           1..35
                       note = IHH-gRNA-R3
source                 1..35
                       mol_type = other DNA
                       organism = synthetic construct
SEQUENCE: 39
ttgtaggcga gcgggatgag cttgcggggc ggccg                              35

SEQ ID NO: 40          moltype = DNA   length = 35
FEATURE                Location/Qualifiers
misc_feature           1..35
                       note = IHH-gRNA-R1
source                 1..35
                       mol_type = other DNA
                       organism = synthetic construct
SEQUENCE: 40
gggccgtacc tgggtcatga gccggtcggc gccgg                              35

SEQ ID NO: 41          moltype = DNA   length = 160
FEATURE                Location/Qualifiers
misc_feature           1..160
                       note = fragment of wild-type IHH
source                 1..160
                       mol_type = other DNA
                       organism = Gallus gallus
SEQUENCE: 41
ccatgaagcc ggcgcggctg ctgctgctgc tgagcgggtg cgcgctgctg ctggcgccgg   60
ccgtgcgctg ctgcggggcg ggcagggttg tgggcagccg ccgccggccg ccccgcaagc  120
tcatcccgct cgcctacaag cagttcagcc ccaacgtgcc                        160

SEQ ID NO: 42          moltype = DNA   length = 160
FEATURE                Location/Qualifiers
source                 1..160
                       mol_type = other DNA
                       organism = Gallus gallus
SEQUENCE: 42
ccatgaagcc ggcgcggctg ctgctgctgc tgagcgggtg cgcgctgctg ctggcgccgg   60
ccgtgcgctg ctgcggggcg ggcagggttg tgggcagccg ccgccggccg ccccgcaagc  120
tcatcccgct cgcctacaag cagttcagcc ccaacgtgcc                        160

SEQ ID NO: 43          moltype = DNA   length = 20
FEATURE                Location/Qualifiers
misc_feature           1..20
                       note = sgRNA R3
source                 1..20
                       mol_type = other DNA
                       organism = Gallus gallus
SEQUENCE: 43
gcgttcgagt agggcgagcg                                               20

SEQ ID NO: 44          moltype = AA    length = 53
FEATURE                Location/Qualifiers
REGION                 1..53
                       note = peptide encoded by SEQ ID NO: 41
source                 1..53
                       mol_type = protein
```

```
                        organism = Gallus gallus
SEQUENCE: 44
MKPARLLLLL SGCALLLAPA VRCCGPGRVV GSRRRPPRKL IPLAYKQFSP NVP          53

SEQ ID NO: 45           moltype = DNA   length = 160
FEATURE                 Location/Qualifiers
misc_feature            1..160
                        note = IHH target sequence - mut1
source                  1..160
                        mol_type = other DNA
                        organism = synthetic construct
SEQUENCE: 45
ccatgaagcc ggcgcggctg ctgctgctgc tgagcgggtg cgcgctgctg ctggcgccgg    60
ccgtgcgctg ctgcgggccg ggcagggttg tggacagccg ccgccggccg ccccgcaagc   120
tcatcccgct cgcctacaag cagttcagcc caacgtgcc                          160

SEQ ID NO: 46           moltype = DNA   length = 160
FEATURE                 Location/Qualifiers
misc_feature            1..160
                        note = IHH target sequence   sanger peak map 1
source                  1..160
                        mol_type = other DNA
                        organism = synthetic construct
SEQUENCE: 46
ccatgaagcc ggcgcggctg ctgctgctgc tgagcgggtg cccgctgctg ctggcgccgg    60
ccgtgcgctg ctgcgggccg ggcagggttg tgggcagccg ccgccggccg ccccgcaagc   120
tcatcccgct cgcctacaag cagttcagcc caacgtgcc                          160

SEQ ID NO: 47           moltype = DNA   length = 158
FEATURE                 Location/Qualifiers
misc_feature            1..158
                        note = IHH target sequence   Sanger peak map 2
source                  1..158
                        mol_type = other DNA
                        organism = synthetic construct
SEQUENCE: 47
ccatgaagcc ggcgcggctg ctgctgctga tggtgagcgc gctgctgctg gtgacggccg    60
tgcgctgctg ccggccggcg cttgttgtcg ggcagccggg cgccggccgc ccccgagctc   120
atcgcgctcg cctaccattc ggtcggcacg cacatacc                           158

SEQ ID NO: 48           moltype = DNA   length = 161
FEATURE                 Location/Qualifiers
misc_feature            1..161
                        note = IHH target sequence   mut3
source                  1..161
                        mol_type = other DNA
                        organism = synthetic construct
SEQUENCE: 48
ccatgaagcc ggcgcggctg ctgctgctgc tgagcgggtg cgcgctgctg ctggcgccgg    60
ccgtgcgctg ctgcagggcc gggcagggtt gtgggcagcc gccgccggcc gccccgcaag   120
ctcatcccgc tcgcctacaa gcagttcagc cccaacgtgc c                       161

SEQ ID NO: 49           moltype = DNA   length = 135
FEATURE                 Location/Qualifiers
misc_feature            1..135
                        note = IHH target sequence   sanger peak map 3
source                  1..135
                        mol_type = other DNA
                        organism = synthetic construct
SEQUENCE: 49
ccatgaagcc ggcgcggctg ctgctgctga tcgggtgcgc gctgctgctg gcgccggccg    60
tgcgctgctg cgggccgggc agggttgtgg gcagccgccg ccggccgccc cgcaagctca   120
tcccgctcgc ctaca                                                    135

SEQ ID NO: 50           moltype = DNA   length = 135
FEATURE                 Location/Qualifiers
misc_feature            1..135
                        note = IHH target sequence   sanger peak map 4
source                  1..135
                        mol_type = other DNA
                        organism = synthetic construct
SEQUENCE: 50
ccatgaagcc ggcgcggctg ctgctgctga tcgggtgcgc gctgctgctg gcgccggccg    60
tgcgctgctg cgggccggcc aggggggtgg ggagccgccg ccggccgccg cgccagctca   120
tccccctcgc ctact                                                    135

SEQ ID NO: 51           moltype = DNA   length = 135
FEATURE                 Location/Qualifiers
misc_feature            1..135
```

|  | note = IHH target sequence    mut2 |
| --- | --- |
| source | 1..135 |
|  | mol_type = other DNA |
|  | organism = synthetic construct |

SEQUENCE: 51

```
ccatgaagcc ggcgcggctg ctgctgctga gcgggtgcgc gctgctgctg gcgccggccg  60
tgcgctgctg cgggccgggc agggttgtgg gcagccgccg ccggccgccc cgcaagctca  120
tcccgctcgc ctaca                                                  135
```

METHOD FOR GENERATING GENOME-EDITED CHICKENS

CROSS-REFERENCE TO RELATED APPLICATION

This patent application is a continuation application of International Patent Application No: PCT/CN2024/106891 filed on Jul. 23, 2024 and claims priority to the Chinese Patent Application No. CN202410931448.9 filed with the China National Intellectual Property Administration (CNIPA) on Jul. 12, 2024, and entitled "METHOD FOR PRODUCING GENE-EDITED CHICKENS", which is incorporated herein by reference in its entirety.

REFERENCE TO SEQUENCE LISTING

A computer readable XML file entitled "GWPCTP20240705146-sequence listing", which was created on Dec. 6, 2024, with a file size of about 61,196 bytes, contains the sequence listing for this application, has been filed with this application, and is hereby incorporated by reference in its entirety.

TECHNICAL FIELD

The present disclosure relates to the technical field of genetic engineering, and in particular to a method for generating gene-edited chickens.

BACKGROUND

As an oviparous animal, chicken embryonic development is divided into two stages: in vivo development and in vitro development. When a hen reaches sexual maturity, the primary follicles in the ovary develop rapidly and gradually increase in size. According to the diameter of the ovarian follicles, the follicles can be divided into prehierarchal follicles such as small white follicles, large white follicles, and small yellow follicles, as well as preovulatory follicles from the first largest follicle with diameter of 40 mm named F1 to the sixth largest follicle with diameter of 10 mm named F6. After ovulation, the F1 follicles are received by the infundibulum of the oviduct and the ovum finishes fertilization at the infundibulum. Then, the yolk carrying the zygote migrates in the oviduct, stays in the magnum for about 4 h to be covered by egg white, stays in the isthmus for about 1 h to complete the deposition of inner and outer eggshell membranes, and then the zygote begins the first mitosis in the isthmus. Next, the egg enters the shell gland and stays here for about 18 h to 19 h to finish eggshell mineralization and pigment deposition. Lastly, the egg is laid from the vagina. At this time, the chicken embryo reaches to blastocyst stage, and including approximately 55,000 cells, specifically a germinal disc with a diameter of about 3.5 mm visible on the surface of the yolk. If fertilized eggs are stored at a low temperature of 16° C., the embryonic development diapauses; if the fertilized eggs are placed back in incubation conditions at 37.8° C., the embryo can restart its development. After a 21-day incubation process, the chicks can hatch.

Since chickens have the above-mentioned unique reproductive physiological characteristics and early zygotes are not easy to obtain, methods applicable to mammals such as micromanipulation of zygotes or somatic cell nuclear transplantation to produce genome-modified individuals cannot be implemented in the chickens. Currently, genome-edited chickens are mainly produced by primordial germ cell (PGC)-mediated method. This method has high requirements on the experimenters and strict demand on laboratory environment. The culture of PGC cells is difficult, the transfection is inefficient, and the transplantation to chicken embryos is also a big challenge, which needs skilled techniques and rich experiences. In addition, due to the competition of endogenous PGCs, the $G_0$ germline transmission efficiency is variable and low (generally less than 10%), and it is spend at least 18 months to obtain homozygous mutants in $G_2$ offspring, which is time-consuming and labor-intensive. At present, the PGC-mediated method can generate sterile surrogate chicken strains. The endogenous PGCs of sterile surrogate chicken embryos with knock-in inducible lethal gene on the DAZL gene locus can be ablated by adding drugs. Then, the injected exogenous donor PGCs can transplant to the gonads of chicken embryos host. Hence, the application of the sterile surrogate chicken can not only improve the $G_0$ germline transmission efficiency, but also shorten to $G_1$ offspring to obtain homozygous mutants. However, the surrogate hosts are transgenic chickens, which poses a hidden danger to biosafety.

SUMMARY

In order to solve the above problems, the present disclosure provides a method for generating a gene-edited chicken. In the present disclosure, ovarian injection in situ of clustered regularly interspaced short palindromic repeats (CRISPR)/CRISPR-associated protein 9 (Cas9) ribonucleoprotein (RNP) is conducted on a hen ($G_{-1}$) through a new approach that is independent of PGC-mediated methods, such that a chimeric chicken with edited somatic cells and gonads can be efficiently obtained in a $G_0$ generation. This is a new method for generating gene-edited chickens that is simple, convenient, safe, and efficient.

To achieve the above objective, the present disclosure provides the following technical solutions.

The present disclosure provides a method for generating gene-edited chickens, including the following steps: injecting a gene editing reagent into ovarian medulla of a hen to obtain a $G_{-1}$ hen; wherein the hen that will lay the first egg after injection of 10 to 15 days are chosen to be operated, and the gene editing reagent includes CRISPR/Cas9 RNP; crossing the $G_{-1}$ hen with wild-type roosters to obtain fertilized eggs, and hatching the fertilized eggs artificially to obtain a $G_0$ population; and detecting gene editing results in the $G_0$ population to obtain the gene-edited chickens.

Preferably, the reagent for gene editing using CRISPR/Cas9 RNP includes Cas9 proteins, guide RNAs (gRNA), and buffers; the Cas9 proteins and the gRNAs are at a molar ratio of 1:(1-2); and the Cas9 proteins are injected at a concentration of 3.5 μg/μL.

Preferably, the buffers include 20 mM of 4-(2-hydroxyethyl)-1-piperazine ethanesulfonic acid (HEPES) and 500 mM of NaCl.

Preferably, the Cas9 proteins include Cas9 protein obtained by using prokaryotic expression system.

Preferably, an editing efficiency of the gRNA is detected using a chicken tool cell line before the gene editing reagent is injected, and then a gRNA with an editing efficiency greater than or equal to 45% is selected.

Preferably, the chicken tool cell line includes DF-1 cells.

Preferably, the hen used to inject with the gene editing reagent are fasted on the day of injection.

Preferably, the method further includes: cockerels and hens among the gene-edited chickens are mated to each other to obtain homozygous mutants.

Preferably, a process of detecting the gene editing result includes steps 1) and/or 2):
1) observing the phenotype of the individual in the $G_0$ offspring according to mutation effect produced by the modified target gene; and
2) detecting gene editing events and mutational types of the individual in the $G_0$ offspring.

Preferably, a process of detecting in 2) includes PCR amplification and/or sequencing.

Beneficial effects: ovarian injection in situ is conducted on a hen, where the gene editing reagents are injected into ovarian medulla of the hen that is close to laying eggs, such that the injected exogenous gene editing reagent can enter developing ovarian follicles through blood circulation. In $G_0$ offspring, chimera chickens with both somatic cells and germ cells edited are successfully and efficiently obtained, with the $G_0$ editing efficiency reaching up to 36.36%. Compared with the traditional primordial germ cell (PGC)-mediated method, the ovarian injection in situ is time-saving and labor-saving, convenient and rapid, low-cost, and highly safe. The specific advantages are reflected in the following aspects: (1) Since the $G_0$ gene-edited chickens obtained by ovarian injection in situ are somatic cell chimeras, mutant individuals can be identified within one week after hatching by extracting genomic DNA from blood, thus shortening the time of identification of mutant individuals. (2) Since the $G_0$ gene-edited chickens obtained by ovarian injection in situ are somatic chimeras, they can show the mutant phenotype of functional genes immediately in the $G_0$ individuals. This makes it possible to determine in advance whether the mutation affects its normal function of the target gene, and is of great significance for the research of novel genes and accelerates the research progress of functional genes. (3) Mutants can be found in both $G_0$ roosters and hens obtained by ovarian injection in situ. After the mutants mature, they are mated with each other, and homozygous mutant individuals can be obtained in the $G_1$ offspring, thus shortening the generation cycle to 8 months. For the individuals, TA cloning results of genomic DNA have showed that the individual mosaic rate is 8.33% to 52.94%, and a target gene site is also detected to be edited in the rooster' semen (FIG. 2). The above results show that there is a high mosaic ratio of $G_0$ individuals, and it is easier to obtain heterozygotes or homozygotes in the $G_1$ offspring. (4) Since the injected gene editing reagent is Cas9 RNP, the Cas9 protein can be degraded after taking effect. In this way, gene editing events can occur without introducing exogenous genes and contaminating the chicken's own genome, thus ensuring biosafety. (5) Furthermore, the method bypasses the process of culturing and transfecting PGCs. After verifying the editing efficiency of the gRNA of target gene at the DF-1 cell line, only the Cas9 protein needs to be expressed and purified and the gRNA needs to be transcribed in vitro before surgical injection. Therefore, the method has a relatively mature process and a simple surgical procedure and is easy to learn. Only a universal animal anesthesia machine, surgical instruments, and 1 mL of a disposable sterile syringe are required to complete the ovarian injection in situ. (6) In addition, the costs of the method are mainly universal animal anesthesia machine, gRNA in vitro transcription kit, identification of the mutants and their feeding making the costs much lower than those of the PGC-mediated method.

In summary, the ovarian injection in situ provided by the present disclosure is expected to replace the traditional PGC-mediated method for generating the gene-edited chicken. The method of the present disclosure can be applied to non-professional laboratories for the study of functional genes, thereby accelerating the research process of the gene-edited chicken.

BRIEF DESCRIPTION OF THE DRAWINGS

To illustrate the embodiments of the present application or the technical solutions in the prior art more clearly, the drawings required in the embodiments will be briefly introduced below.

FIG. 1A-FIG. 1D show a gRNA design targeting the Indian Hedgehog (IHH) gene and the detection results of editing efficiency in DF-1 cells.

DETAILED DESCRIPTION OF THE EMBODIMENTS

Figure 1D:
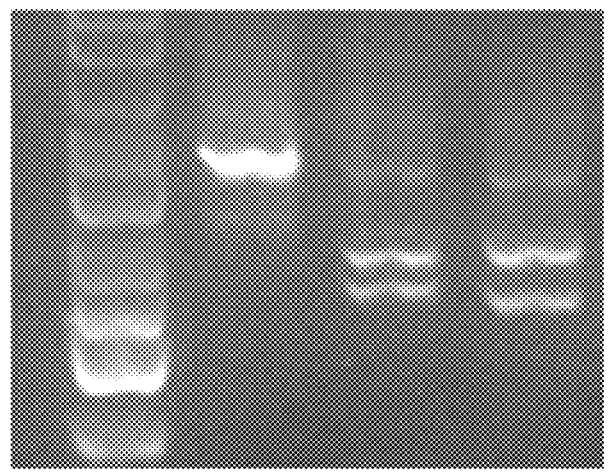

The present disclosure provides a method for generating gene-edited chickens, including the following steps: injecting a gene editing reagent into ovarian medulla of a hen to obtain a $G_{-1}$ hen; where the hen that will lay the first egg after injection of 10 to 15 days are chosen to be operated; the genome editing reagent includes a reagent for gene editing using CRISPR/Cas9 RNP; crossing the G. 1 hen with wild-type roosters to obtain fertilized eggs, and hatching the fertilized eggs artificially to obtain a $G_0$ population; and detecting gene editing results in the $G_0$ population to obtain the gene-edited chickens.

In the present disclosure, a gene editing reagent is injected into ovarian medulla of a hen 10 days to 15 days before laying the first egg to obtain a $G_{-1}$ hen. The gene editing reagent includes a reagent for gene editing using CRISPR/Cas9 RNP; the reagent for gene editing using CRISPR/Cas9 RNP preferably includes a Cas9 protein and a gRNA; the Cas9 protein is preferably injected at a concentration of 3.5 µg/µL; the Cas9 and the gRNA are at a molar ratio of preferably 1:(1-2), more preferably 1:1. When injecting Cas9 RNP, a buffer (Storage Buffer) preferably includes the following components at the final concentrations: 20 mM of HEPES and 500 mM of NaCl. On the day of injection, the Cas9 protein and the gRNA are preferably prepared immediately after thawing, and the reagent is prepared in a centrifuge tube, incubated at 37° C. for 5 min, and then transferred into a disposable sterile syringe to ensure that the Cas9 RNP is injected into the ovary of the hen within 1 h. If there are two or more gRNAs, each of the gRNAs is preferably incubated with an equal volume of the Cas9 protein to form RNPs and then mixed and transferred into a disposable sterile syringe for ovarian injection.

In the present disclosure, a candidate gRNA is preferably designed according to the target gene. The activity of the candidate gRNA is preferably identified on a chicken tool cell line, and a gRNA with an editing efficiency of not less than 45% is preferably selected to ensure that the target gRNA used for ovarian injection in vivo can achieve gene editing. This step is to screen for gRNAs with higher activity at the cellular level. The chicken tool cell line preferably includes a DF-1 cell line.

In the present disclosure, a large amount of the gRNA is preferably prepared by in vitro transcription. Two 10 µL in vitro transcription reaction systems can meet the gRNA injection requirements for one chicken. Preferably, the Cas9 protein is prepared by prokaryotic expression and the Cas9 protein is purified by Ni-NTA affinity chromatography, which is not only low-cost but also allows for designing different forms of Cas9 fusion proteins as needed.

In the present disclosure, after obtaining the Cas9 protein and the gRNA, in vitro cleavage is preferably conducted to verify the activity of the Cas9 protein and the gRNA. There are certain requirements for the age and ovarian development status of the hens to be injected. The hens that are close to laying eggs (hens 10 days to 15 days before laying eggs), about 15 to 17 weeks old, are selected depending on the breed of the hens selected. The advantages of selecting hens that are close to laying eggs are: 1) the ovarian follicles of hens close to laying have not yet developed into pre-ovulatory ovarian follicles. When the ovarian injection is conducted, there may be no pre-ovulatory ovarian follicles hindering operative view formed by the surgical incision, making it easy to find the location of the ovaries and determine the position when injecting exogenous materials, which is conducive to the injection operation. 2) When the ovarian follicles of hens close to laying egg, the ovary develops into small yellow follicles and large yellow follicles, the oocyte enter into the rapid yolk deposition phase. The injected exogenous protein is more easily taken up by the ovarian follicles and the $G_0$ editing efficiency can be improved at this time.

In the present disclosure, the injection (ovarian injection in situ) is preferably conducted in the morning and hens to be operated on are preferably fasted on the same day of the operation. This is to prevent the full intestine from hindering the surgical view formed by the incision and to prevent accidents during the operation. The specific method is preferably step 7 in Example 1. The injection has low operating threshold and can be conducted by any technician in the field without the need for professional personnel to operate.

In the present disclosure, after a $G_{-1}$ hen is obtained and the $G_{-1}$ hen lays the first egg, the $G_{-1}$ hen is inseminated artificially to obtain fertilized eggs. The fertilized eggs are artificially hatched to obtain the $G_0$ population. The injection on the hens does not affect the fertility rate and hatchability rate of the eggs.

In the present disclosure, after obtaining the $G_0$ population, gene editing events in the $G_0$ population are detected to obtain the gene-edited chicken. A process of detecting the gene editing events preferably includes: after hatching, detecting the offspring of the operated $G_{-1}$ hens at both phenotypic and genetic levels. Phenotypically, the phenotype of the individuals in the $G_0$ population is preferably observed based on mutation effect produced by the modified functional gene. At the genetic level, blood is preferably collected from 1-day-old chicks by the carotid artery blood sampling to extract genomic DNA, and the gRNA site of the target gene is amplified by PCR. The gene-edited individual is identified using LabChip® GXII Touch microfluidic capillary electrophoresis system, and the HT DNA High Sensitivity Labchip® and supporting reagents are preferably used. The Indel types of the edited individuals are detected using TA cloning and other methods, and the edited individual is confirmed to be kept for breeding. Thus, a chimeric chicken is obtained in the $G_0$ individuals, in which both somatic cells and germ cells are edited.

In the present disclosure, the method further preferably includes: mating $G_0$ roosters with $G_0$ hens each other among the gene-edited chicken to obtain homozygous gene-edited chickens.

In order to further illustrate the present disclosure, the method for generating gene-edited chickens provided by the present disclosure will be described in detail below in conjunction with accompanying drawings and examples, but they should not be construed as limiting the protection scope of the present disclosure.

Example 1

In nature, the loss of a single copy of the IHH gene causes the Xingyi bantam chicken to exhibit a creeping phenotype, characterized by pronounced chondrodystrophy characteristic with short shanks and small wings. This mutation can be identified in the embryonic stage. Homozygous deletion of the IHH gene can cause chicken embryo death during early embryonic development, indicating that mutation of the IHH gene can affect embryonic development and exhibit an easily observed mutant phenotype. The IHH gene as a target gene facilitates to screen edited individuals from a phenotypical perspective.

1. gRNA design and vector construction: in order to disturb the function of the chicken IHH gene as much as possible, 2 gRNA combinations targeting the first exon of the chicken IHH gene were designed to achieve fragment knockout. Three gRNA sites were designed, where gRNA-R1 was located at the end of the first exon, and gRNA-R2 and gRNA-R3 were located at the front end and middle end of the first exon, respectively. The gRNA-R1 was separately combined with gRNA-R2 and gRNA-R3 (represented as IHH-gR2+gR1 and IHH-gR3+gR1) to construct a pX330-dual gRNA knockout plasmid. The sequences and positions of the gRNA are shown in FIG. 1A and FIG. 1B, specifically: gRNA-R1: 5'-tacctgggtcatgagccggt-3' (SEQ ID NO: 1); gRNA-R2: 5'-cggcggcaataaatagcgaa-3' (SEQ ID NO: 2); gRNA-R3: 5'-gcgagcgggatgagcttgcg-3' (SEQ ID NO: 3).

A construction process of the pX330-dual gRNA knockout plasmid included: (1) when a pX330-dual gRNA knockout vector was first constructed, sequences that could transcribe the dual gRNAs were obtained by gene synthesis, specifically:

IHH-gR2+gR1: 5'-ATCGGAAGACCT-CACCGcggcggcaataaatagcgaaGTTT-TAGAGCTAGAAATAGCAAGTTAAAA TAAGGCTAGTCCGTTATCAACTT-GAAAAAGTGGCACCGAGTCGGTGCTTTTTT-GAGGGC CTATTTCCCATGATTCCTTCATATTTG-CATATACGATACAAGGCTGTTAGAGAGATAAT-TGG AATTAATTTGACTGTAAACACAAAGAT-ATTAGTACAAAATACGTGACGTAGAAAGTAATA ATTTCTTGGGTAGTTTGCAGTTTTAAAAT-TATGTTTTAAAATGGACTATCATATGCTTACCG TAACTTGAAAGTATTTCGATTTCTTGGCTT-TATATATCTTGTGGAAAGGACGAAACACCGt acctgggtcatgagccggtGTTTGGGTCTTCATCG-3' (SEQ ID NO: 4);

IHH-gR3+gR1: 5'-ATCGGAAGACCTCACCgcgagcgg-gatgagcttgcgGTTTTAGAGCTAGAAATAGCAAGT-TAAAAT AAGGCTAGTCCGTTATCAACTT-GAAAAAGTGGCACCGAGTCGGTGCTTTT- TTGAGGGCC TATTTCCCATGATTCCTTCATAT-TTGCATATACGATACAAGGCTGTTAGAGAGA-TAATTGGA ATTAATTTGACTGTAAACACAAA-GATATTAGTACAAAATACGTGACGTAGAAAG-TAATAA TTTCTTGGGTAGTTTGCAGTTT-TAAAATTATGTTTTAAAATGGACTAT-CATATGCTTACCGT AACTTGAAAGTATTTCGAT-TTCTTGGCTTTATATATCTTGTGGAAAGGAC-GAAACACCGta cctgggtcat-gagccggtGTTTGGGTCTTCATCG-3' (SEQ ID NO: 5).

The sequences shown in SEQ ID NO: 4 and SEQ ID NO: 5 were cloned into a pUC57 vector separately, and the vector was used as a template for PCR amplification of dual gRNA.

(2) The dual-gRNA transcript sequences were amplified by PCR using KOD One™ PCR Master Mix (TOYOBO), where primer sequences included: IHH-gR2+gR1-F: 5'-atcggaagacct-caccgcggcggcaataaatagcgaagttttagagctagaaatag-3' (SEQ ID NO: 6); IHH-gR2+gR1-R: 5'-cgatgaagacc-caaacaccggctcatgacccaggtacggtgtttcgtcctttcc-3' (SEQ ID NO: 7); IHH-gR3+gR1-F: 5'-atcggaagacct-caccgcgagcgggatgagcttgcggttttagagctagaaatag-3' (SEQ ID NO: 8); the primer sequence of IHH-gR3+gR1-R was shown in SEQ ID NO: 7.

(3) The pX330 linearized vector obtained by BbsI digestion and the PCR product of the dual gRNAs treated with BbsI were ligated with T4 ligase. The ligated products were transformed into *Escherichia coli* DH5a competent cells, and single clones were identified by Sanger sequencing. The endotoxin-free plasmids were extracted from successful recombinant bacterial cultures to obtain knockout vectors pX330-gRNA-(R2+R1) and pX330-gRNA-(R3+R1).

2. DF-1 cell transfection: chicken DF-1 cells were recovered and cultured. The day before transfection, the DF-1 cells were seeded into a 6-well plate. On the next day, when the cell confluence reached to 60% to 70%, The two kinds of pX330-dual gRNA vectors constructed in step 1 were co-transfected with PiggyBac transposon plasmids and transposase plasmids into DF-1 cells, respectively, with a mass ratio of 3:3:1. Transfection was conducted using a FuGENE® HD transfection reagent (PROMEGA) according to the instructions. After 48 h, 1.5% puromycin was used to screen positive cells. After 3 days, when all negative cells died, the cells were collected and the genomic DNA was extracted. Primers were designed to amplify the fragments containing gRNA target sites, where the primer sequences were: F: 5'-aatttcccctctcactcc-3' (SEQ ID NO: 9); R: 5'-ctttgccatcctactctg-3' (SEQ ID NO: 10).

The editing efficiency of different gRNA combinations was detected by 1.5% agarose gel electrophoresis, and the results are shown in FIG. 1C. The fragment deletion efficiency of the gRNA-R1 and gRNA-R3 combination was 48.4%, while the fragment deletion efficiency of the gRNA-R1 and gRNA-R2 combination was 23.8%. Therefore, the gRNA-R1 and gRNA-R3 combination with a higher editing efficiency was selected for ovarian injection in vivo.

3. Preparation of gRNA: the above 2 gRNAs were respectively cloned into the linearized pX330 vector obtained by BbsI digestion to obtain pX330-gR1 and pX330-gR3 plasmids. The plasmids were used as templates for PCR amplification, where an upstream primer contained a T7 promoter and the gRNA sequence, and a downstream primer included ployA sequence and the partial reverse complementary sequence of the gRNA scaffold on the pX330 vector, specifically:

T7_IHH_gR1_F: 5'-TAATACGACTCAC-TATAGGGtacctgggtcatgagccggt-3' (SEQ ID NO: 11); T7_IHH_gR3_F: 5'-TAATACGACTCAC-TATAGGGgcgagcgggatgagcttgcg-3' (SEQ ID NO: 12); the sequence of T7_uni_R was 5'-AAAAAAgcaccgactcggtgc-cac-3' (SEQ ID NO.13);

5'-TAATACGACTCACTATAGGG-3' (SEQ ID NO: 14) in the upstream primer was the T7 promoter sequence, AAAAAA in the downstream primer was the polyA tail sequence as a transcription termination sequence, and 5'-gcaccgactcggtgccac-3' (SEQ ID NO: 15) was a partial sequence of the gRNA scaffold.

The PCR product was purified to serve as DNA templates for gRNA in vitro transcription. According to the instructions of a MEGAshortscript™ T7 transcription kit (THERMO FISHER SCIENTIFIC, catalog number AM1354), the gRNA was purified using phenol-chloroform method and the obtained gRNA was dissolved in nuclease-free water. The concentration and OD value of gRNA were measured by NanoDrop™ 2000, where the concentration of gRNA is (1-5) μg/μL, and could satisfy the injection requirements.

4. Preparation of Cas9 protein: the 2NLS sequence was gene-synthesized and cloned into the pET28a-Cas9 plasmid (ADDGENE plasmid, #53261) to obtain the pET28a-Cas9-2NLS plasmid. The construction process of the pET28a-Cas9-2NLS prokaryotic expression vector included: (1) vector linearization: the pET28a-Cas9 plasmid was double-digested with MreI and XhoI, and the digested product was then performed gel purification. (2) PCR amplification of partial Cas9 sequence: primers Cas9-tyF: 5'-caagcg-catgctggccagcgccggcgagctgcagaagggca-3' (SEQ ID NO: 16) and Cas9-tyR: 5'-tctcgtacagaccggt-gatgctctggtggatcagggtg-3' (SEQ ID NO: 17) were designed and synthesized, and a part of the Cas9 sequence in the pET28a-Cas9 plasmid was PCR-amplified using KOD One™ PCR Master Mix, and the product was purified. (3) 2NLS sequence gene synthesis and PCR amplification: the 2NLS sequence was gene-synthesized and cloned into a pUC57 vector backbone; where the 2NLS sequence was as follows: 5'-cat-caccggtctgtacgagacccgcatcgacct-gagccagctgggcggcgacggcggctccggacctccaaagaaaaa-gagaaaagtaga ggacccaaagaaaaagagaaaagtatacccc-tacgacgtgcccgactacgcctgttaactcgagcaccac-3' (SEQ ID NO: 18). Using this as the PCR template, primers 2NLS-tyF: 5'-catcaccggtctgtacgagacccgcatcgacctga-3' (SEQ ID NO: 19) and 2NLS-tyR: 5'-cagtggtggtggtggtggtgctcgagttaacaggcgtagtcgg-3' (SEQ ID NO: 20) were designed and synthesized, and PCR amplification was conducted using KOD One™ PCR Master Mix, and the product was purified. (4) Homologous recombination: pEASY®-Basic Seamless Cloning and Assembly Kit (Beijing TransGen Biotech Co., Ltd.) was used to insert partial Cas9 sequence and 2NLS sequence into the pET28a-Cas9 linearized vector by homologous recombination. Transformation, single clone identification, and plasmid extraction were then conducted to obtain the pET28a-Cas9-2NLS prokaryotic expression vector, which was used for prokaryotic expression and purification of the target protein.

The pET28a-Cas9-2NLS prokaryotic expression vector was transformed using the BL21(DE3) *Escherichia coli* strain and then plated onto LB agar plates containing 50 g/ml kanamycin and incubate at 37° C. overnight. Single clones were picked and transferred to 20 mL of 2×YT medium containing 50 g/ml kanamycin, and then incubate at 37° C. with shaking at 200 rpm overnight. The culture was transferred into 1 L of 2×YT medium containing 50 g/ml kanamycin and was continue to be shaken at 200 rpm and 37° C. until $OD_{600}$ value reaches about 0.6. Then the culture was allowed to return to room temperature for 30 min, and 0.5 M IPTG solution was added to make a final concentration of 0.5 mM. The culture was then incubated at 16° C. and 120 rpm for 20 h. The obtained culture was centrifuged at 8,000 g for 10 min at 4° C. to harvest bacterial cell pellet, and the bacterial cell pellet were added with a lysis buffer (20 mM Tris-HCl, 500 mM NaCl, 10% glycerol, 0.1% Trixon λ-100, 1 mg/mL lysozyme, and 1 mM PMSF) to lyse the cells by sonication, and then centrifuged at 12,000 rpm and 4° C. for 30 min to collect a supernatant, which contained soluble Cas9-2NLS proteins.

The supernatant was combined with Ni Sepharose™ 6 Fast Flow filler (CYTIVA) at 4° C. for 1 h and eluted with 10, 20, 50, 100, and 250 mM imidazole buffers separately. The 250 mM imidazole buffer (20 mM Tris-HCl, 500 mM NaCl, and 250 mM imidazole) was collected and a 50-kDa MWCO concentration column was used to exchange the buffer of the purified protein with storage buffer. When the volume of the solution in the concentration column was less than 500 μL, the protein storage buffer (20 mM HEPES, 500 mM NaCl) was added to exchange the imidazole buffer, and centrifuged at 4,000 g and 4° C. until the volume of the solution was less than 1 mL. The solution was transferred into a 1.5 mL centrifuge tube and the concentration of Cas9-2NLS protein was determined with the Bradford assay. The protein was aliquot according to the amount used for each chicken, and then quickly frozen in liquid nitrogen and stored at −80° C. Generally, 1 clone was inoculated into 1 L of 2×YT medium, and the Cas9 protein produced by the cultured bacterial cells could satisfy the injection dosage of 2 to 3 hens.

5. In vitro cleavage activity assessment: the target sequence containing gRNA site was amplified from the chicken genomic DNA, and the PCR product was purified. 200 ng of PCR product, 400 ng of gRNA, 1 μg of Cas9 protein, and 2 μL of 10× Reaction Buffer were added to a 20 μL reaction system. The reaction mixture was incubated at 37° C. for 1 h and then at 70° C. for 10 min. The product was detected by 1.5% agarose gel electrophoresis. The results are shown in FIG. 1D.

6. Preparation of Cas9 RNP: a 200 μL reaction system included 3.5 μg/μL of Cas9 protein, equimolar volumes of gRNA-R1 and gRNA-R3 (a molar ratio of Cas9 protein to gRNA was 1:1), 20 mM of HEPES, and 500 mM of NaCl. Each gRNA was mixed with an equal molar of Cas9 protein in a volume of 100 μL and incubated at 37° C. for 5 min to form RNPs, and two kinds of Cas9 RNP were mixed to 200 μL and transferred into a 1 mL disposable sterile syringe.

7. Ovarian injection in situ: (1) hens that were close to laying eggs were selected. In this example, 16-weeks-old hens with developing small yellow follicles were selected for injection. (2) The ovarian injection in situ was conducted in the morning, and the hen was fasted on the day of operation. Before the operation, an anesthetic (ketamine, mixed with saline in a volume ratio of 1:3, injection volume: 0.05 mL to 0.08 mL) was injected into the breast muscle of the hen to allow muscle anesthesia. When the hen was tired, the tip of an endotracheal tube was inserted into the trachea of the hen, and the tail of the endotracheal tube was connected to a universal animal anesthesia machine (R620-S1-IECS, RWD LIFE SCIENCE) to provide the hen with a mixed gas of oxygen and isoflurane. The hen was held by two operators, where one held the head and wings of the hen, while the other held legs of the hen and assisted the third operator to conduct the ovarian injection in situ operation. The left side body of the hen was allowed to face the third operator upward. The feathers on the front side of the left leg of the hen were plucked, an opening position was determined, and a line was drawn at the front edge of the left leg, skin was cut at the line with a scalpel, and hemostatic forceps were pierced between the last but one and the last but two ribs to form a 2 cm long incision, and the incision was expanded by a distractor to expose a field of vision. The peritoneum or air sac of the hen was cut with a scalpel, and a membrane structure was cut on the surface of ovary to expose the ovary. The reagent for gene editing using CRISPR/Cas9 RNP was injected into the ovarian medulla using a 1 mL disposable sterile syringe with an extended syringe needle, where multiple-point injections were adopted generally, with an injection volume of 200 μL for about 15 injections. The distractor was removed, the incision was sutured with an absorbable surgical suture, and the resulting wound was wiped with iodine to allow disinfection. The hens that underwent the operation were given water and feed after they regained consciousness and continued to be raised in single cages normally.

8. Incubation of fertilized eggs and detection: incubation of eggs: the hens were raised in single cages normally after the ovarian injection in situ was conducted. After the hens laid the first egg, they were inseminated with pooled semen. After the first insemination, fertilized eggs were collected from the 3rd day and the hens were inseminated every 5 days. A batch of fertilized eggs was hatched every 7 days, with a total of 6 to 8 batches. The incubator was set at a constant temperature (37.8° C.) and constant humidity (60%) with turning the eggs every 2 h. The eggs were transferred to a hatcher tray on the 18th day of incubation and the chicks will hatch on the 22nd day. When they hatch, a wing number was placed on the right wing of the newborn chicks to distinguish them from each other.

Sample collection and DNA extraction: leg tissue or gonad tissue of chicken embryos was obtained on the 12.5 embryonic days to detect gene editing events. Blood was collected from 1-day-old chicks by carotid artery method after hatching. Genomic DNA was extracted using the cell/tissue/blood genomic DNA extraction kit (TIANGEN Biotech (Beijing) Co., Ltd.). The leg tissue or blood was added to 200 μL of GA solution, and then ground using a homogenizer after adding grinding beads. 220 μL of a mixed solution of proteinase K and GB solution was added; and after sufficient oscillation, the resulting mixture was bathed in 70° C. water and incubated for 2 h to 3 h, and the subsequent genomic DNA extraction operation was conducted according to the instructions.

PCR amplification: detection of gene editing events was conducted on individuals with obvious mutation phenotypes. The extracted genomic DNA was used as a template and PrimeSTAR® HS DNA Polymerase with GC Buffer (TAKARA) was used to amplify the IHH-gR3 target site using specific primers. The specific primer sequences were: F: 5'-gcccttcgctatttattg-3' (SEQ ID NO: 21); R: 5'-cgtgagctccttgaagcg-3' (SEQ ID NO: 22). A LabChip™ GXll Touch microfluidic capillary electrophoresis system was used to identify whether mutations occurred.

TA cloning: PrimeSTAR® HS DNA Polymerase with GC Buffer (TAKARA) was used to amplify the genomic DNA of the individuals with mutations, where primer pairs included F: 5'-gcccttcgctatttattgccgc-3' (SEQ ID NO: 23); R: 5'-ggataaactcgctgctctgccca-3' (SEQ ID NO: 24). A PCR product was purified, and a corresponding system was prepared using pEASY®-Blunt Cloning Kit (Beijing Trans-Gen Biotech Co., Ltd.), and incubated at 37° C. to allow cloning. The colones were picked for Sanger sequencing and the sequencing results were aligned with the reference sequence. The partial results are shown in Table 1.

TABLE 1

Detection results of TA cloning

| Individual No. | No. of TA clones | No. of mutations | Mutation ratio |
|---|---|---|---|
| 3-28 | 17 | 9 | 52.94% |
| 3-30 | 24 | 2 | 8.33% |
| 4-22 | 20 | 4 | 20.00% |

Table 1 shows that the individual mosaicism rate was at 8.33% to 52.94%.

Figure 2:
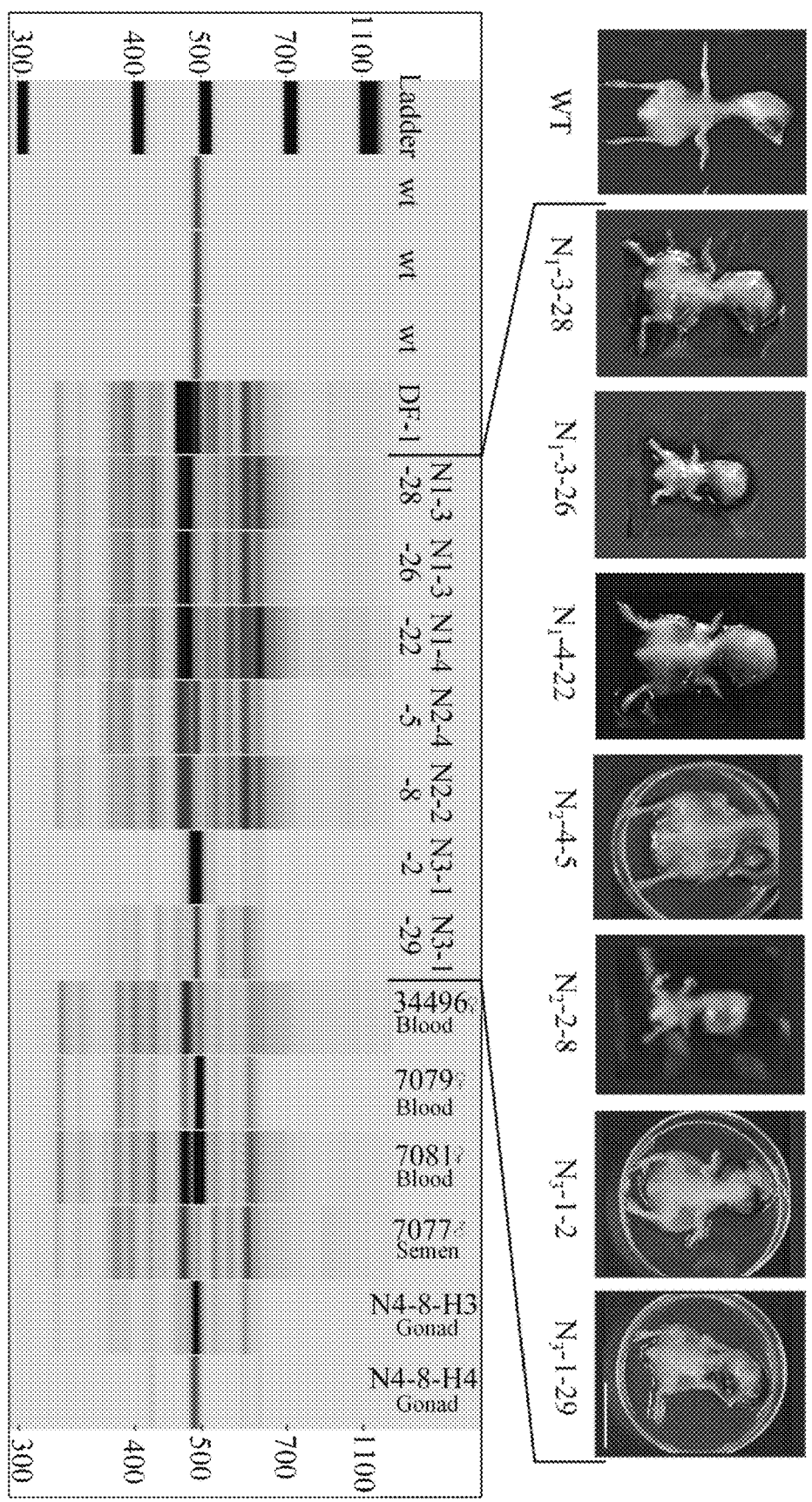
FIG. 2 shows the phenotypes of some IHH mutants and the editing detection results of the gRNA-R3 target site.
Figure 3A:
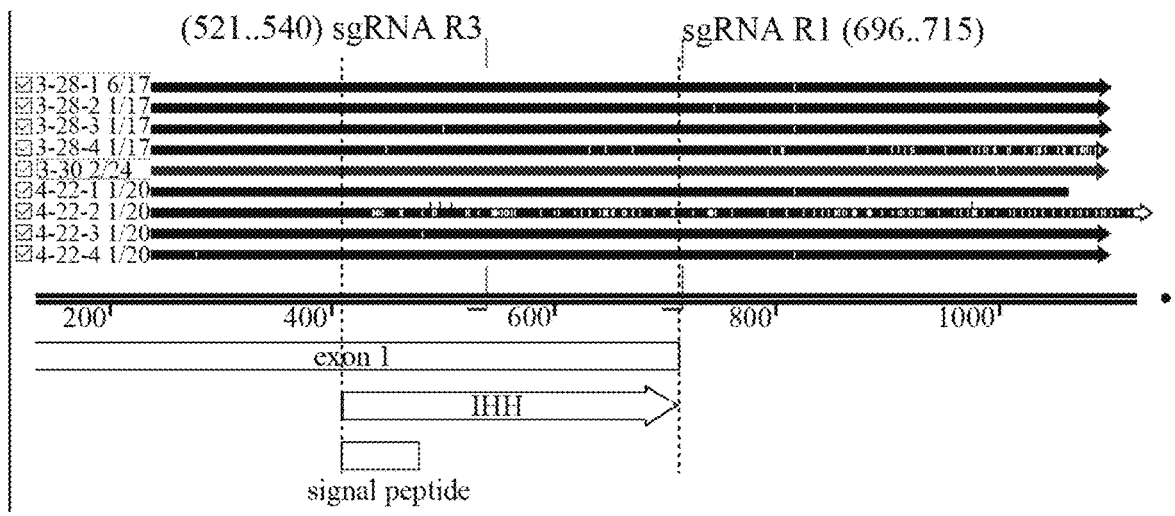
FIG. 3A-FIG. 3D show the TA cloning results of the IHH gene mutants.
Figure 3B:
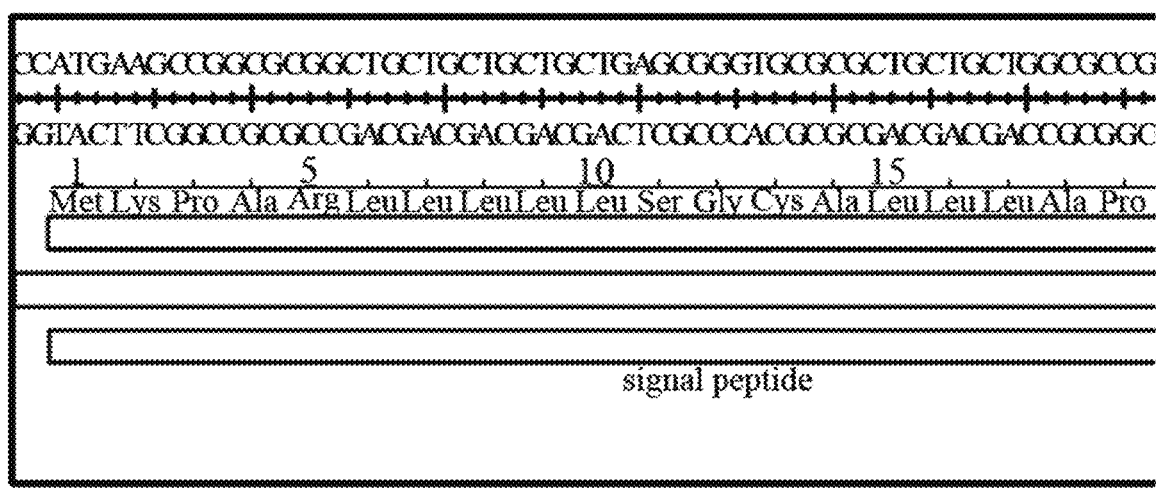
Figure 3C:
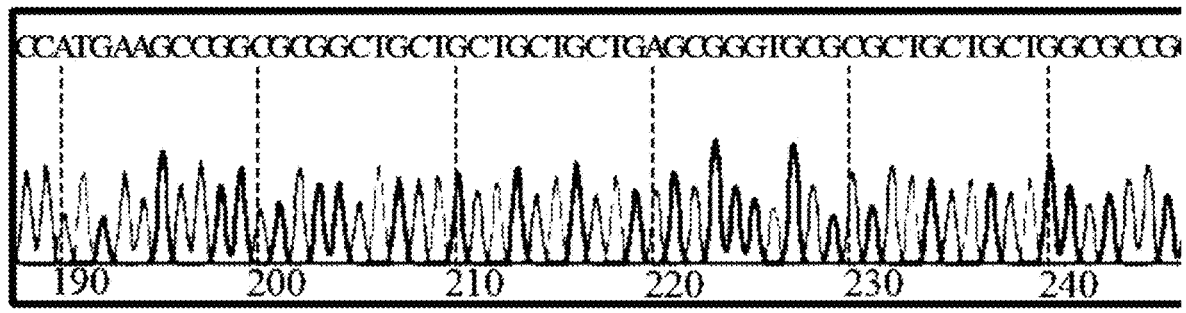
Figure 3C:
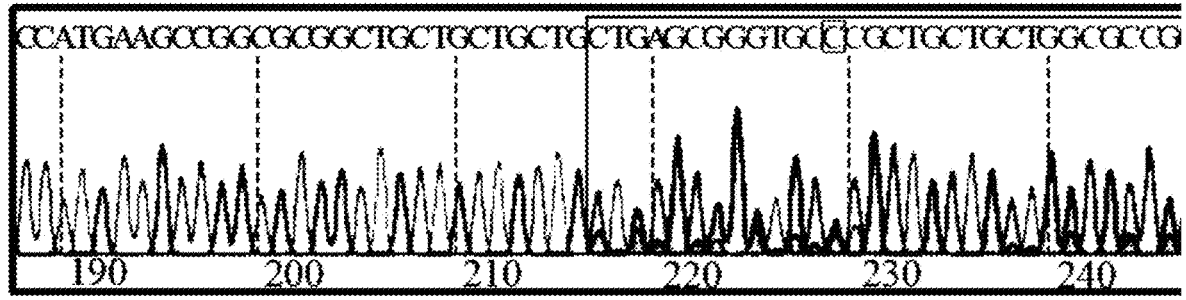
Figure 3D:
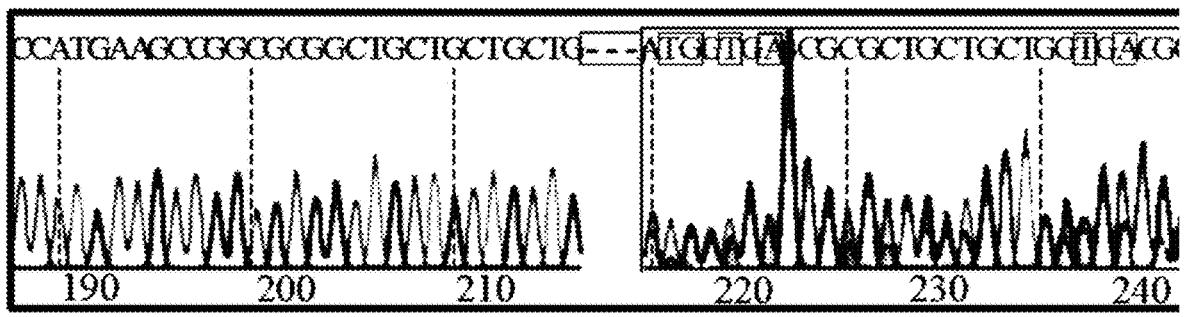
Figure 3D:
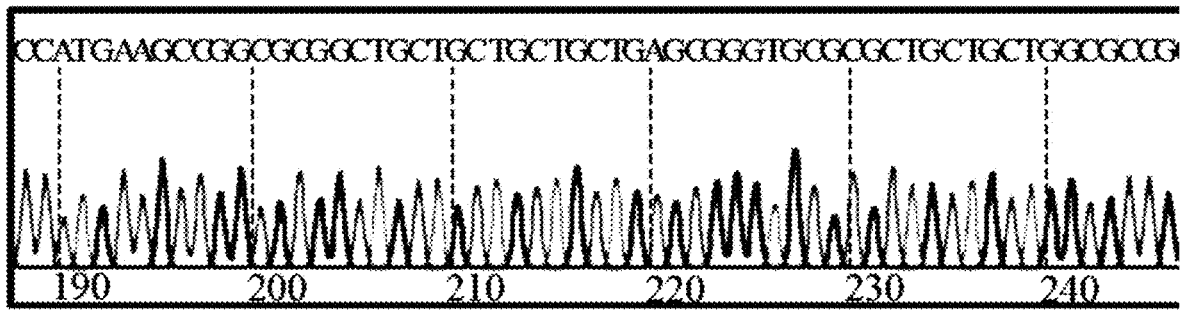

9. Ovarian injection editing results: Embryonic detection: chicken embryo phenotype and IHH gene editing were detected in the embryonic stage, and the results were shown in FIG. 2 and FIGS. 3A-3D. In FIG. 2, wt represented the wild-type; DF-1 represented the positive control; numbers starting with N represented embryonic detection, and DNA template for PCR amplification not specified was extracted from the leg tissue; numbers 34496, 7079, and 7081 represented blood genomic DNA from 3 edited hens raised to sexual maturity; 7077 represented 1 edited rooster raised to sexual maturity, and its semen genomic DNA was extracted for detection. $G_0$ chicken embryos showed abnormal phenotypes such as early death, transparent edema, limb dysplasia, and eye dysplasia (FIG. 2). These results showed that these individuals had undergone gene editing (FIG. 2, FIGS. 3A-3D), indicating that the obtained by ovarian injection in situ could obtain $G_0$ gene-edited individuals with immediate manifestation of mutant phenotypes in. The gonads of chicken embryos were also edited, indicating that both the somatic cells and germ cells of the gene-edited individuals obtained by ovarian injection in situ were edited. According to statistics, in the case of using the ovarian injection in situ to target the IHH gene for editing, the gene editing efficiency of the $G_0$ offspring could reach up to 36.36% for the injected hens (Table 2).

TABLE 2

$G_0$ editing efficiency of ovarian injection in situ of Cas9 RNP targeting chicken IHH gene

| Hen No. | No. of eggs | No. of unfertilized eggs | No. of fertilized eggs | Fertility rate | No. of $G_0$ mutants | $G_0$ editing efficiency |
|---|---|---|---|---|---|---|
| A1 | 4 | 0 | 4 | 100.00% | 1 | 25.00% |
| A2 | 41 | 1 | 40 | 97.56% | 11 | 27.50% |
| A3 | 32 | 0 | 32 | 100.00% | 2 | 6.25% |
| A4 | 32 | 0 | 32 | 100.00% | 1 | 3.13% |

TABLE 2-continued $G_0$ editing efficiency of ovarian injection in situ of Cas9 RNP targeting chicken IHH gene

| Hen No. | No. of eggs | No. of unfertilized eggs | No. of fertilized eggs | Fertility rate | No. of $G_0$ mutants | $G_0$ editing efficiency |
|---|---|---|---|---|---|---|
| A5 | 6 | 0 | 6 | 100.00% | 1 | 16.67% |
| A6 | 24 | 2 | 22 | 91.67% | 8 | 36.36% |
| A7 | 35 | 3 | 32 | 91.43% | 2 | 6.25% |
| A8 | 24 | 1 | 23 | 95.83% | 8 | 34.78% |
| Total | 198 | 7 | 191 | 96.46% | 34 | 17.80% |

Individual detection of chicks: some of the fertilized eggs were incubated until they hatched, and some of the chickens were raised until they reached sexual maturity. Currently, 4 chimeras were obtained, including 3 hens and 1 rooster. After detection, the blood of the hens and the semen of the roosters were edited (FIG. 2) and left for mating with each other to obtain next generation.

Comparative Example 1

In situ injection of the pX330 gene-editing plasmid into the ovaries of hens could also obtain chimeras in the $G_0$ individuals in which both somatic cells and germ cells were edited, but the editing efficiency in the $G_0$ individuals was low, at 1.71%. Since pX330 contained the Cas9 gene sequence, $G_0$ individuals could carry the Cas9 gene. The specific plan was as follows:

1. Ovarian injection in situ: pX330-gRNA-(R2+R1) and pX330-gRNA-(R3+R1) knockout vectors obtained in step 1 of Example 1 were directly injected into the ovaries of hens according to the ovarian injection in situ in step 7. The pX330-gRNA-(R3+R1) plasmid was set to injection dose of 100 μg/hen (hens numbered A10 to A19) and 200 g/hen (hens numbered A20 to A29), with 10 hens in each treatment; while the pX330-gRNA-(R2+R1) plasmid was injected into the ovaries of 2 hens, with an injection dose of 100 g/hen (hens numbered S11 and S12).

2. Incubation of fertilized eggs and detection: the incubation of fertilized eggs was the same as that in Example 1. Sample collection and DNA extraction were the same as those in Example 1. Cas9 gene detection: the extracted blood genomic DNA was used as a template to allow PCR amplification of the Cas9 gene with specific primers using PrimeSTAR® HS (Premix), where the primer sequences included: Cas9-F: 5'-cctgagcgaactggataaggcc-3' (SEQ ID NO: 25), Cas9-R: 5'-ctcttggcgatcatcttccgca-3' (SEQ ID NO: 26).

PCR amplification of IHH target gene: for Cas9 positive individuals, PrimeSTAR® HS DNA Polymerase with GC Buffer was used to amplify the sequence including the two target sites with specific primers. Agarose gel electrophoresis was used to detect whether the pX330 plasmid injected into the ovaries in vivo could produce fragment deletions. The primer sequences were as follows: for the treatment of hen ovary injection of pX330-gRNA-(R2+R1) plasmid, the sequences of the detection primer pair are shown in SEQ ID NO: 9 and SEQ ID NO: 10; for the treatment of hen ovary injection of pX330-gRNA-(R3+R1) plasmid, the sequences of the detection primer pair are shown in SEQ ID NO: 21 and SEQ ID NO: 22.

T7E1 assay detection: for Cas9-positive individuals, the editing events of a single gRNA site were detected using a T7E1 assay. The fragments containing the target sites gRNA-R1, gRNA-R2, and gRNA-R3 were PCR amplified using genomic DNA as a template and the corresponding specific primers. The amplified products were digested with T7E1 enzyme, and the results of 1.5% agarose gel electrophoresis was performed color invert using ImageJ software to analyze the mutant ratio. Primer sequences are shown in Table 3.

TABLE 3

Primer sequences for T7E1 assay

| Primer name | Primer sequence (5'-3') | SEQ ID NO: | Product length (bp) |
|---|---|---|---|
| IHH-gR1-F2 | gctcatcccgctcgcctacaa | 27 | 655 |
| IHH-gR1-R2 | ggataaactcgctgctctgccca | 24 | |
| IHH-gR3-F | gcccttcgctatttattg | 21 | 472 |
| IHH-gR3-R | cgtgagctccttgaagcg | 22 | |
| IHH-gR2-F | atctcttcaatttcccctctcac | 28 | 456 |
| IHH-gR2-R | gcacccgctcagcagcagcagca | 29 | |

TA cloning: TA cloning in Example 1 was conducted on the mutant individuals confirmed by T7E1.

Figure 4:
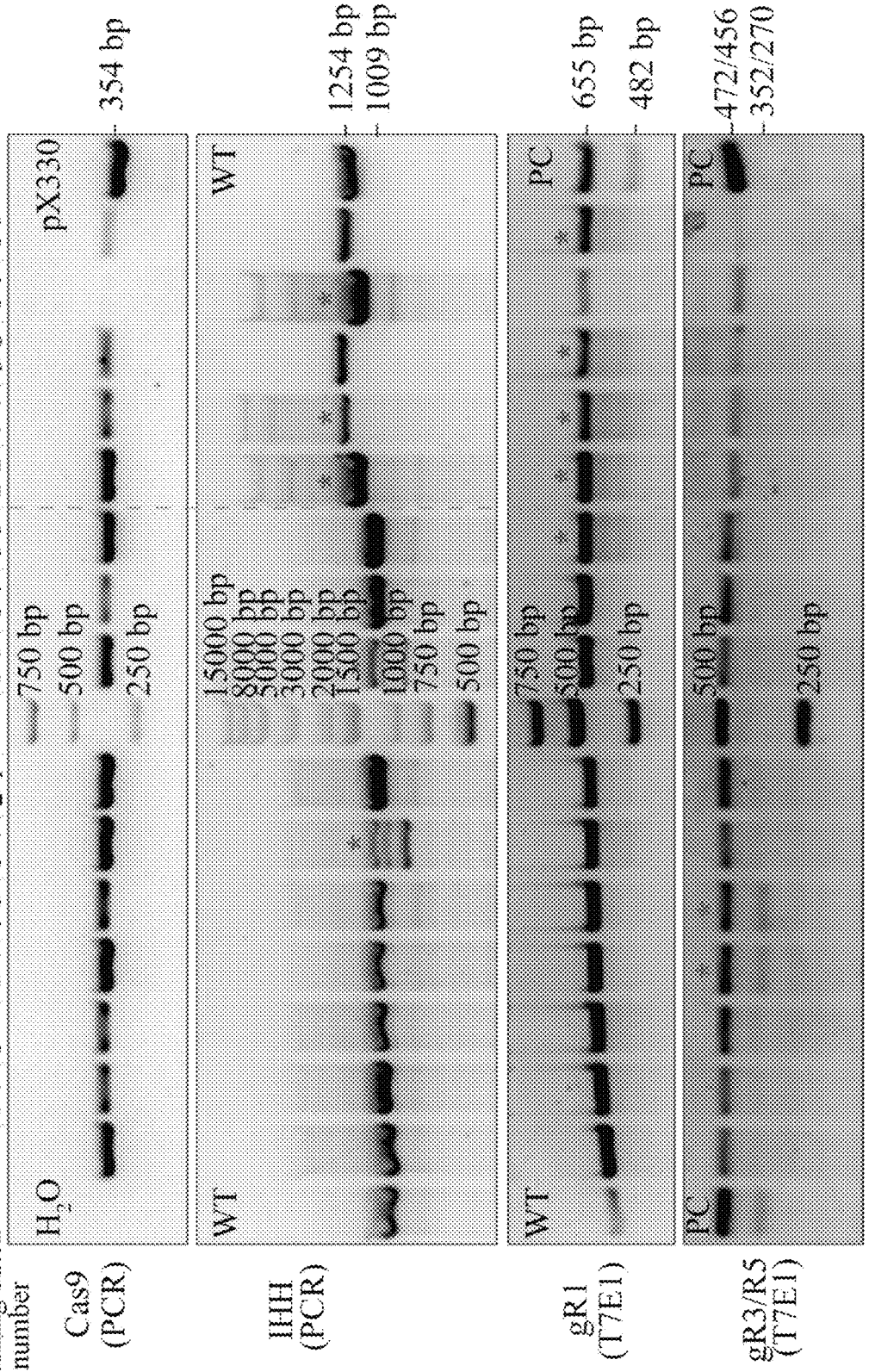
FIG. 4 shows the detection results of gene editing in the $G_0$ individuals of hens injected with pX330 plasmid in their ovaries.

3. Results of editing events: the gene editing results of the $G_0$ individuals by injecting the pX330 plasmid into the hen's ovary are shown in FIG. 4 and Table 4, where the $G_0$ individuals without "$G_0$ chick wing number" but with "hatching batch number" were dead embryos that were not successfully hatched. PCR was conducted on the Cas9 and IHH gene to detect the modification of these 2 genes in the $G_0$ individual. In the treatment of plasmid, the size of PCR fragment of the IHH gene was 1,009 bp, and 1254 bp in the treatment of pX330-gRNA-(R3+R1) and pX330-gRNA-(R2+R1) plasmid, respectively. T7E1 assays were performed on the PCR products of gRNA-R1, gRNA-R3, and gRNA-R2 target sequences with lengths of 655, 472, and 456 bp, respectively. Asterisks indicated gene-edited individuals.

gRNA-(R3+R1) plasmid injection, 5 individuals were gene edited, among which 2 unhatched embryos (A16-3-4, A25-3-5) had obvious fragment deletions, 1 embryo (6100) had a mutation at the gRNA-R1 target site, and 2 chicks (50981, 50980) had a mutation at the gRNA-R3 target site. In the treatment of pX330-gRNA-(R2+R1) plasmid injection, gene editing occurred in 5 individuals, of which 2 chicks (60935, 50976) had fragment deletions, and 4 chicks (60935, 60957, 50954, 50955) had mutations at the gRNA-R1 target site (FIG. 4 and Table 4). The above results showed that increasing the plasmid dosage could not significantly improve the Cas9 positivity rate in the $G_0$ offspring, and the choice of gRNA combination could affect the editing efficiency of fragment deletion, and not both gRNAs could work at the same time.

Figure 5A:
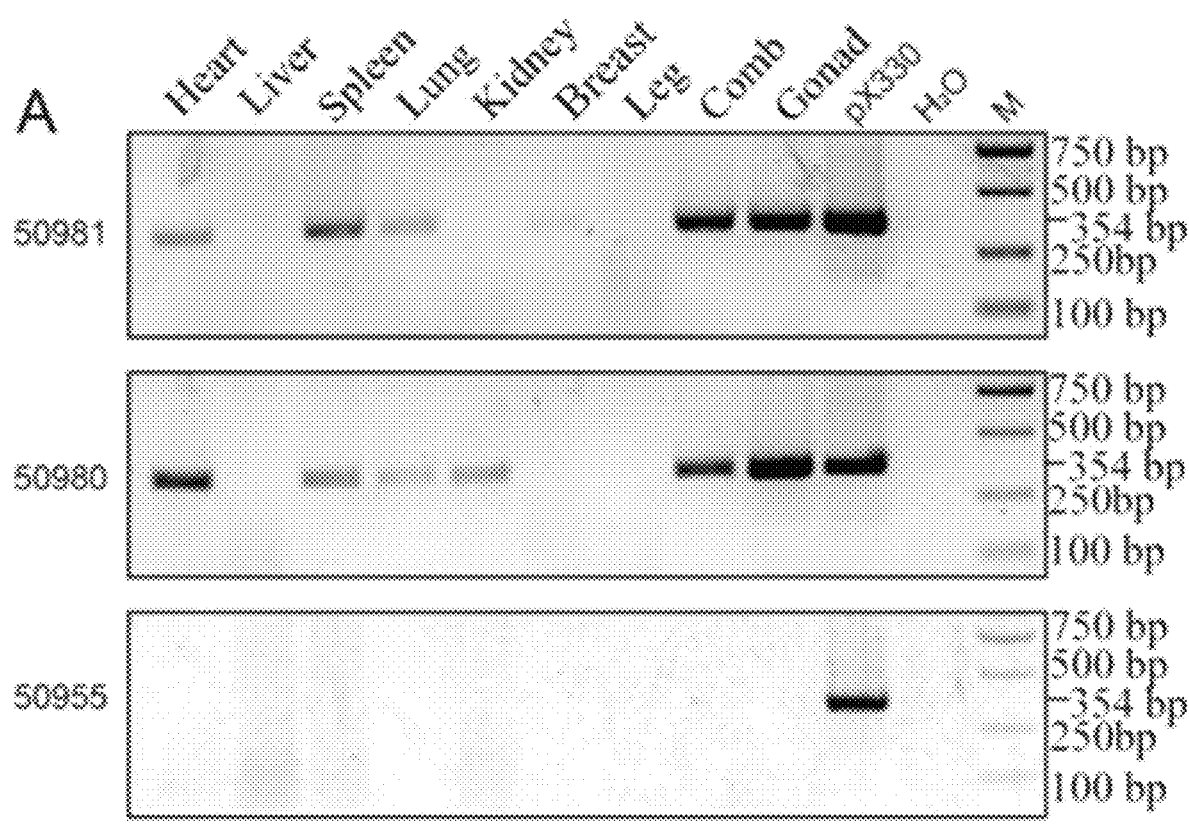
FIG. 5A-FIG. 5E show the detection results of Cas9 gene in different tissues and IHH gene editing in gonads of $G_0$ mutant individuals.
Figure 5B:
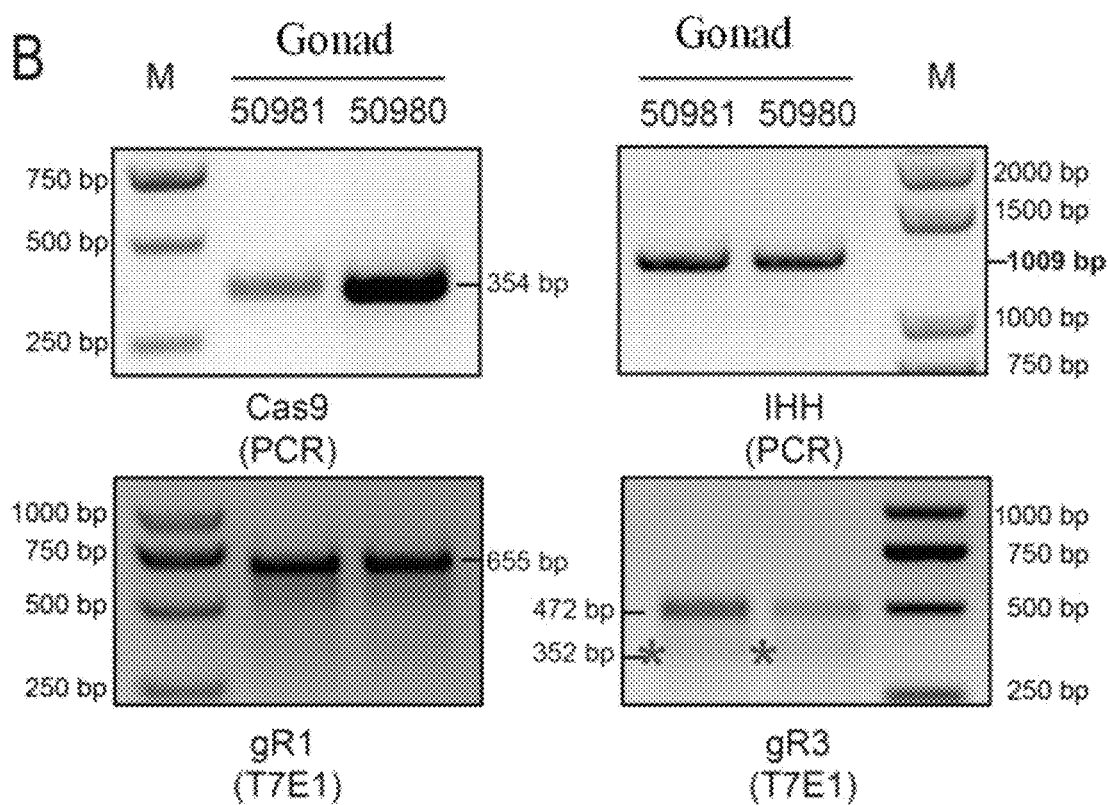
Figure 5C:
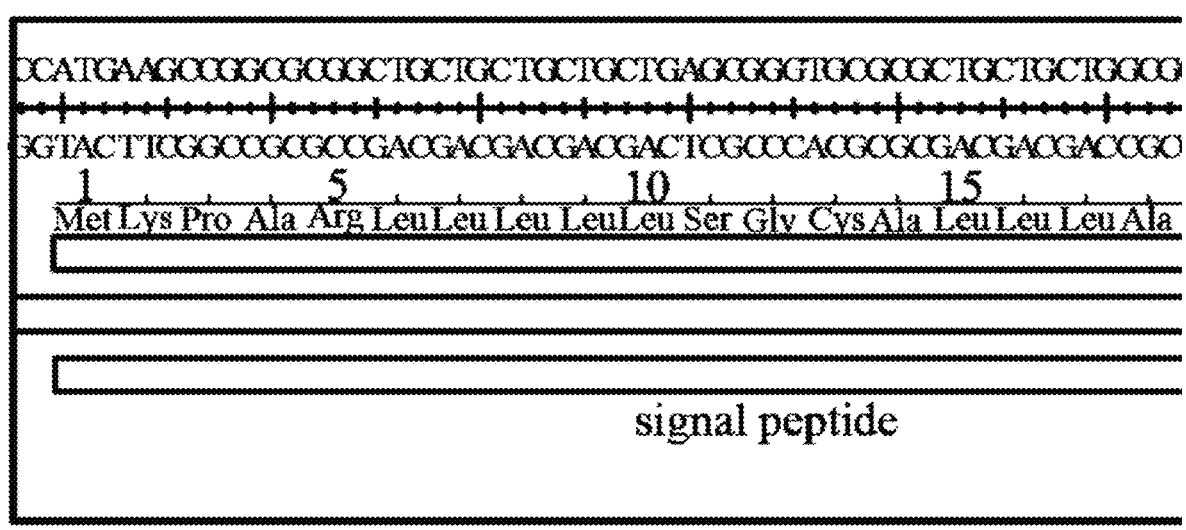
Figure 5D:
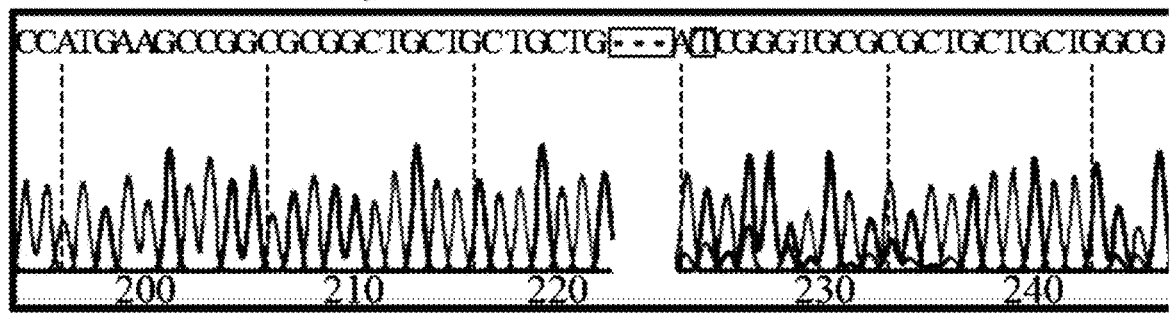
Figure 5D:
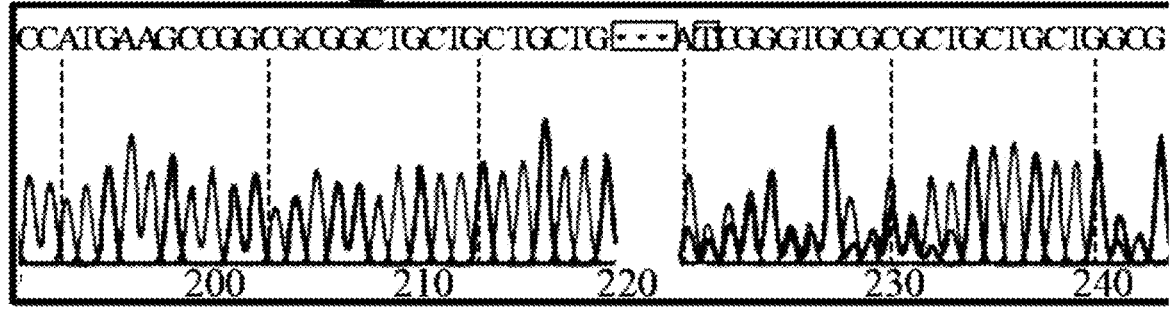
Figure 5E:
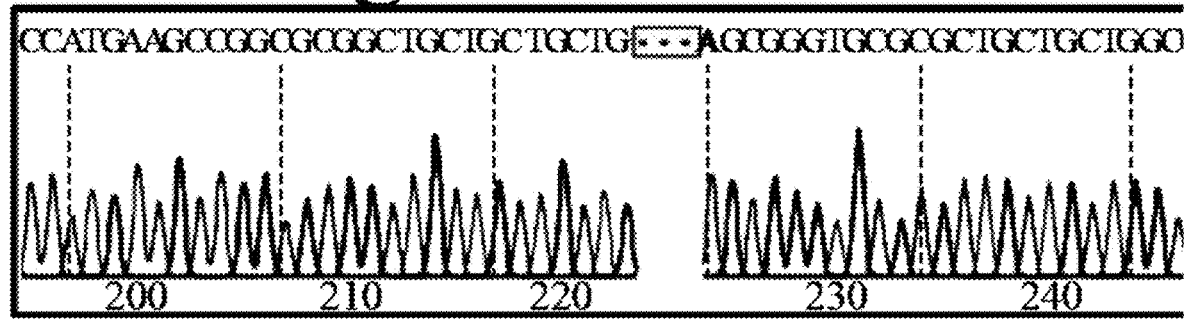
Figure 5E:
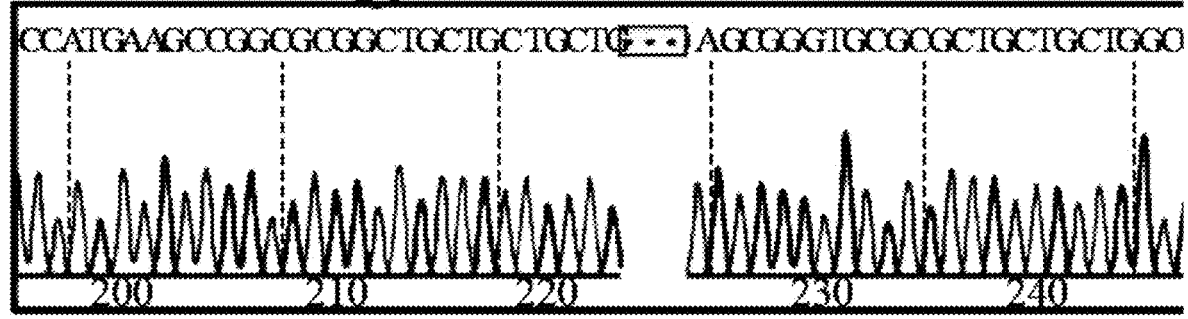

In order to detect whether the Cas9 gene also existed in other tissues, 9 tissues including heart, liver, spleen, lung, kidney, breast muscle, leg muscle, comb, and gonad were collected from 3 chicks (50980, 50981, and 50955), and genomic DNA was extracted and the Cas9 gene was amplified. The results are shown in FIG. 5A, where pX330 plasmid and $H_2O$ were used as DNA templates for positive and negative controls, respectively. The Cas9 gene was detected in the heart, spleen, lung, comb, and gonad of chicks 50980 and 50981 (FIG. 5A), indicating that the 2 chicks were chimeras; while the Cas9 gene was not detected in the tissues of chick 50955. Since the gRNA-R3 target site was edited in the blood of individuals 50980 and 50981, in order to evaluate whether the editing could be inherited to the next generation ($G_1$), the gonads of these 2 chickens were used to detect whether the gRNA-R3 and gRNA-R1 target sites were mutated. The results of T7E1 assay showed that only the gRNA-R3 target site was mutated in these 2 individuals, which was consistent with the detection results in the blood (FIG. 5B). The Sanger sequencing results also showed that these 2 individuals had a 3-bp deletion in the signal peptide sequence upstream of the gRNA-R3 target site, resulting in loss of the 10th amino acid leucine (FIG.

TABLE 4

$G_0$ editing efficiency of ovarian injection in situ of pX330 plasmid targeting chicken IHH gene

| Injected plasmid | Dosage (μg/hen) | No. of hens injection | Injection volume (μL) | No. of eggs | No. of $G_0$ chicks | Fertility rate | No. of dead embryos (embryo, %) | $G_0$ individuals carrying Cas9 (No., %) | No. of $G_0$ chimeras (No., %) |
|---|---|---|---|---|---|---|---|---|---|
| pX330-gRNA-(R3 + R1) | 100 | 10 | 200 | 311 | 250 | 80.39% | 21(8.40%) | 7(2.80%) | 3(1.20%) |
| pX330-gRNA-(R3 + R1) | 200 | 10 | 400 | 332 | 277 | 83.43% | 14(5.05%) | 3(1.08%) | 2(0.72%) |
| pX330-gRNA-(R2 + R1) | 100 | 2 | 200 | 60 | 55 | 91.67% | 8(14.55%) | 4(7.27%) | 5(9.09%) |
| Total | — | 22 | — | 703 | 582 | 82.79% | 43(7.38%) | 14(2.40%) | 10(1.71%) |

As shown in FIG. 4, 14 $G_0$ chicks or embryos were detected to carry the Cas9 gene, of which 11 were from the 100 μg/hen treatment and 3 were from the 200 μg/hen treatment, indicating that the efficiency of $G_0$ offspring carrying the Cas9 gene was higher when the injection dose was 100 μg/hen.

In the treatments with plasmid injection doses of 100 μg/hen and 200 μg/hen, gene editing events was detected in 8 (2.62%) and 2 (0.72%) individuals, respectively, indicating that the injection dose of 100 μg/hen had a higher efficiency in the $G_0$ offspring. In the treatment of pX330-

5C), which might affect the secretion of IHH protein. These results suggested that it was feasible to create gene-edited chickens by ovarian injection in situ, but the editing efficiency required to be further improved.

Example 2

Compared with Example 1, except for the different Cas9 proteins used for ovarian injection, the other steps were the same. A construction process of the pET28a-4NLS-Cas9-2NLS prokaryotic expression vector included:

(1) Vector linearization: the pET28a-Cas9-2NLS prokaryotic expression vector was digested with NdeI and KpnI, and the digestion products were purified. (2) 4NLS sequence amplification: the 4NLS sequence was synthesized by Beijing Tsingke Biotech Co., Ltd. and cloned into the pUC57 vector backbone. The 4NLS sequence was as follows: 5'-cagccatatgcc-caagaaaagcgcaaagtgggtggcagcccgaagaagaagcg-caaagtgggcggcagtccgaaaaagaaacgcaaag tgggcggtagcccgaagaagaagcgcaaagtgggtatc-cacggtgtcccagcagccaccatggacaagaagtacag-catcggcctggacat cggtaccaacagc-3' (SEQ ID NO: 30). Using this plasmid as a PCR template, primers 4NLS-F: 5'-ggaattccatatgcccaagaaaaagcga-3' (SEQ ID NO: 31) and 4NLS-R: 5'-cggggtaccgatgtccaggccga-3' (SEQ ID NO: 32) were designed and synthesized. KOD One™ PCR Master Mix was used for PCR amplification, purification, followed by double restriction digestion with NdeI and KpnI, purification. (3) Ligation and cloning: the T4 ligase was used to allow ligation and cloning to obtain the pET28a-4NLS-Cas9-2NLS prokaryotic expression vector.

The protein purification of 4NLS-Cas9-2NLS was the same as that of Cas9-2NLS in Example 1.

The effects of ovarian injection in situ of 4NLS-Cas9-2NLS RNP are shown in Table 5.

TABLE 5

$G_0$ editing efficiency of injection of 4NLS-Cas9-2NLS RNP targeting chicken IHH gene

| Hen No. | No. of eggs | No. of unfertilized eggs | No. of fertilized eggs | Fertility rate | No. of $G_0$ mutants | $G_0$ editing efficiency |
|---|---|---|---|---|---|---|
| B1 | 40 | 1 | 39 | 97.50% | 0 | 0.00% |
| B2 | 33 | 1 | 32 | 96.97% | 2 | 6.25% |
| B3 | 36 | 0 | 36 | 100.00% | 1 | 2.78% |
| B4 | 43 | 3 | 40 | 93.02% | 3 | 7.50% |
| B5 | 34 | 6 | 28 | 82.35% | 5 | 17.86% |
| B6 | 36 | 0 | 36 | 100.00% | 9 | 25.00% |
| B7 | 14 | 3 | 11 | 78.57% | 1 | 9.09% |
| B8 | 30 | 5 | 25 | 83.33% | 7 | 28.00% |
| Total | 266 | 19 | 247 | 92.86% | 28 | 11.34% |

Tables 1 and 5 show that Cas9 protein was not limited to proteins using 2 nuclear localization signals, and similar effects could be achieved using 4NLS-Cas9-2NLS.

Example 3

A method similar to Example 1 was adopted, except that Cas9 RNP was prepared as follows: 41.27 mg of chloroquine diphosphate (SIGMA ALDRICH) was dissolved in 1 mL of Cas9 protein buffer (20 mM HEPES, 500 mM NaCl) to a concentration of 80 mM. When preparing Cas9-2NLS RNP, the corresponding volume was calculated such that the final concentration of chloroquine diphosphate was 2 mM, and the protein was prepared immediately before use and placed at room temperature away from light. The editing results are shown in Table 6.

TABLE 6

$G_0$ editing efficiency of injection of Cas9-2NLS RNP (2 mM chloroquine diphosphate) targeting chicken IHH gene

| Hen No. | No. of eggs | No. of unfertilized eggs | No. of fertilized eggs | Fertility rate | No. of $G_0$ mutants | $G_0$ editing efficiency |
|---|---|---|---|---|---|---|
| C1 | 32 | 0 | 32 | 100.00% | 3 | 9.38% |
| C2 | 24 | 2 | 22 | 91.67% | 0 | 0.00% |
| C3 | 36 | 0 | 36 | 100.00% | 5 | 13.89% |
| C4 | 33 | 1 | 32 | 96.97% | 1 | 3.13% |
| C5 | 32 | 0 | 32 | 100.00% | 0 | 0.00% |
| C6 | 34 | 0 | 34 | 100.00% | 3 | 8.82% |
| C7 | 32 | 0 | 32 | 100.00% | 0 | 0.00% |
| C8 | 13 | 2 | 11 | 84.62% | 0 | 0.00% |
| Total | 236 | 5 | 231 | 97.88% | 12 | 5.19% |

As shown in Table 6, when an endosomal escape agent such as chloroquine diphosphate was added to the buffer during the preparation of Cas9 RNP, the $G_0$ editing efficiency was not affected.

Example 4

A method similar to Example 1 was adopted, except that Cas9 protein used for ovarian injection was a recombinant fusion protein of Cas9 and fluorescent protein expressed by the pET28a-Cas9-mNG prokaryotic expression vector. A construction process of the pET28a-Cas9-mNG prokaryotic expression vector included:

(1) Vector linearization: the procedures were the same as step 4 in Example 1. (2) PCR amplification of Cas9 sequence was similar to step 4 in Example 1, except that the primers were Cas9-mNG-CF (SEQ ID NO: 16) and Cas9-mNG-CR: 5'-gtcgtagggggtatactttctcttttctttgggtcctc-tactttctcttttcttt-3' (SEQ ID NO: 33). (3) PCR amplification of mNG sequence: the G4S*2-mNG-NLS sequence was synthesized by Beijing Tsingke Biotech Co., Ltd. and cloned into the pUC57 vector backbone, where G4S was a flexible linker of GGGGS (SEQ ID NO: 34), G was glycine, and S was serine. 2 G4S flexible linkers were added to reduce the interference between Cas9 and mNG proteins in spatial conformation, and NLS was a nuclear localization signal. The G4S*2-mNG-NLS sequence was as follows: 5'-ggtggtggcggtagcggcggcggcggtagtatggtcagcaaagg-cgaagaggacaacatggcaagtctgccggcaacccacgaactgcat attttggcagcatcaacggcgtcgacttcgatatggtaggt-caaggtaccggtaatccgaacgacggttacgaagagctgaacct-gaagagca ccaaaggcgatctgcaatttagtccgtggattctggttccgca-cattggttacggcttccatcagtatctgccgtatccggacggtatgagtccgttt caggcagcgatggtagatggttctggttatcaggtccatcgtac-catgcagtttgaagacggcgcaagtctgaccgttaactatcgctacacctac gaaggcagccatatcaaaggcgaagcgcaggt-taaaggtaccggttttccggctgacggtccggttatgac-caatagtctgaccgctgctgatt ggtgtcgtagcaaaagacc-tacccgaacgacaagaccatcatctccaccttcaagtggagctacacca-ccggtaacggtaaacgctatcgta gtaccgcacgtaccacc-tataccttttgctaaaccgatggcggcgaactatctgaaaaaccaacc-gatgtacgtcttccgcaagaccgaactgaa gcacagcaaaaccgagct-gaacttcaaagaatggcagaaagcgttcaccgacgttatgggtatgg-acgaactgtacaagccgaagaagaagc gcaaagtg-3' (SEQ ID NO: 35). Using this plasmid as a PCR template, primers Cas9-mNG-mF: 5'-gaaaagtatacccctacgcgtgcccgac-tacgcctgtggtggtggcggtagcggcggc-3' (SEQ ID NO: 36) and Cas9-mNG-mR:

5'-ggtggtggtggtggtgctcgagcactttgcgcttcttcttcggcttgta-cagttcgtcc-3' (SEQ ID NO: 37) were designed and synthesized. The mNG sequence was amplified by PCR using KOD One™ PCR Master Mix, and the product was purified. (4) Homologous recombination: pEASY®-Basic Seamless Cloning and Assembly Kit (Beijing TransGen Biotech Co., Ltd.) was used to clone partial Cas9 sequence obtained in step (2) and mNG sequence obtained in step (3) into the pET28a-Cas9 linearized vector by homologous recombination. Transformation, single clone identification, and plasmid extraction were then conducted to obtain the pET28a-Cas9-mNG prokaryotic expression vector.

The protein purification of Cas9-mNG was the same as that of Cas9-2NLS in Example 1.

The effects of ovarian injection in situ of Cas9-mNG RNP are shown in Table 7.

TABLE 7

$G_0$ editing efficiency of ovarian injection in situ of Cas9-mNG RNP targeting chicken IHH gene

| Hen No. | No. of eggs | No. of unfertilized eggs | No. of fertilized eggs | Fertility rate | No. of $G_0$ mutants | $G_0$ editing efficiency |
|---|---|---|---|---|---|---|
| CNG-1 | 49 | 1 | 48 | 97.96% | 4 | 8.33% |
| CNG-2 | 45 | 1 | 44 | 97.78% | 1 | 2.27% |
| CNG-3 | 34 | 0 | 34 | 100.00% | 9 | 26.47% |
| CNG-4 | 43 | 1 | 42 | 97.67% | 6 | 14.29% |
| CNG-5 | 45 | 0 | 45 | 100.00% | 1 | 2.22% |
| Total | 216 | 3 | 213 | 98.61% | 21 | 9.86% |

As shown in Table 7, the Cas9 protein was fused with a fluorescent protein, such as mNeongreen, to form the Cas9-mNG protein that could also achieve similar gene editing effects.

Although the present application has been described in detail through the above examples, the examples are merely some rather than all of the examples of the present application. All other examples obtained by a person based on these examples without creative efforts shall fall within the protection scope of the present application.

What is claimed is:

1. A method for generating a gene-edited chicken with a IHH gene knockout, comprising the following steps:

injecting a gene editing reagent into ovarian medulla of a hen 10 days to 15 days before the hen lays egg such that a $G_{-1}$ hen is obtained, artificially inseminating the $G_{-1}$ hen such that fertilized eggs are obtained, and artificially hatching the fertilized eggs such that a $G_0$ population is obtained; and detecting gene editing results in the G0 population to identify the gene-edited chicken;

wherein the gene editing reagent comprises a Cas9 protein, at least two guide RNA (gRNA), and a buffer, and the Cas9 protein and each gRNA of the at least two gRNA form a ribonucleoprotein (RNP);

wherein a combined editing efficiency of the at least two gRNA is detected using a chicken tool cell line before the gene editing reagent is injected, and wherein the at least two gRNA have a combined editing efficiency greater than or equal to 45%;

wherein each gRNA of the at least two gRNA target sequences are in the IHH gene; and wherein the at least two gRNA comprise the nucleotide sequences set forth in SEQ ID NO: 1 and SEQ ID NO: 3.

2. The method according to claim 1, wherein the Cas9 protein and the gRNA are at a molar ratio of 1:(1-2), and the Cas9 protein is injected at a concentration of 3.5 μg/μL.

3. The method according to claim 1, wherein the buffer comprises 20 mM of 4-(2-hydroxyethyl)-1-piperazine ethanesulfonic acid (HEPES) and 500 mM of NaCl.

4. The method according to claim 1, wherein the buffer comprises 20 mM of 4-(2-hydroxyethyl)-1-piperazine ethanesulfonic acid (HEPES) and 500 mM of NaCl.

5. The method according to claim 1, wherein the Cas9 protein is isolated from prokaryotic cells expressing the Cas9 protein and purified by Ni-NTA affinity chromatography.

6. The method according to claim 1, wherein the chicken tool cell line comprises DF-1 cells.

7. The method according to claim 1, wherein the hen injected with the gene editing reagent is fasted on the same day of the injection.

8. The method according to claim 1, further comprising: mating a $G_0$ gene-edited rooster obtained from the method of claim 1 with a $G_0$ gene-edited hen obtained from the method of claim 1 such that a homozygous gene-edited chicken is obtained.

9. The method according to claim 1, wherein a process of detecting the gene editing result comprises steps 1) and/or 2):

1) observing a phenotype of an individual in the $G_0$ population according to a mutation effect produced after the gene editing; and 2) determining a gene editing event and a mutant type of the individual in the $G_0$ population.

10. The method according to claim 9, wherein a process for the determining in step 2) comprises PCR amplification and/or sequencing.

* * * * *